US011021507B2

(12) United States Patent
Li et al.

(10) Patent No.: US 11,021,507 B2
(45) Date of Patent: Jun. 1, 2021

(54) MYRICETIN DERIVATIVE AND PREPARING METHOD THEREOF, AND APPLICATION OF SAME FOR TREATING COLITIS, PREVENTING AND TREATING COLITIS TUMORIGENESIS, AND TREATING COLORECTAL CANCER

(71) Applicant: MARINE BIOMEDICAL RESEARCH INSTITUTE OF QINGDAO CO., LTD., Shandong (CN)

(72) Inventors: Wenbao Li, Shandong (CN); Xianjun Qu, Shandong (CN); Feng Li, Shandong (CN); Liang Zhang, Shandong (CN); Shixiao Wang, Shandong (CN); Zhiyu Song, Shandong (CN); Feng Wang, Shandong (CN); Chong Yang, Shandong (CN); Huashi Guan, Shandong (CN)

(73) Assignee: MARINE BIOMEDICAL RESEARCH INSTITUTE OF QINGDAO CO., LTD., Shandong (CN)

( * ) Notice: Subject to any disclaimer, the term of this patent is extended or adjusted under 35 U.S.C. 154(b) by 9 days.

(21) Appl. No.: 16/324,679

(22) PCT Filed: Aug. 4, 2017

(86) PCT No.: PCT/CN2017/095925
§ 371 (c)(1),
(2) Date: Feb. 11, 2019

(87) PCT Pub. No.: WO2018/028511
PCT Pub. Date: Feb. 15, 2018

(65) Prior Publication Data
US 2019/0185506 A1 Jun. 20, 2019

(30) Foreign Application Priority Data
Aug. 12, 2016 (CN) .......................... 201610665566.5

(51) Int. Cl.
| C07H 17/07 | (2006.01) |
| A61K 31/7048 | (2006.01) |
| A61P 35/00 | (2006.01) |
| A61P 1/00 | (2006.01) |
| A61P 1/04 | (2006.01) |
| C07D 311/64 | (2006.01) |
| C07H 1/00 | (2006.01) |

(52) U.S. Cl.
CPC ......... *C07H 17/07* (2013.01); *A61K 31/7048* (2013.01); *A61P 1/00* (2018.01); *A61P 1/04* (2018.01); *A61P 35/00* (2018.01); *C07D 311/64* (2013.01); *C07H 1/00* (2013.01); *Y02P 20/55* (2015.11)

(58) Field of Classification Search
None
See application file for complete search history.

(56) References Cited

U.S. PATENT DOCUMENTS

2015/0182621 A1* 7/2015 Wu .................. A61K 39/39
424/186.1

FOREIGN PATENT DOCUMENTS

| CN | 102698275 A | 10/2012 |
| CN | 105017357 A | 11/2015 |
| DE | 4034586 A1 * | 5/1992 ............. C07H 17/07 |

OTHER PUBLICATIONS

Hiermann, A., Schramm, H. W., & Laufer, S. (1998). Anti-inflammatory activity of myricetin-3-O-β-D-glucuronide and related compounds. Inflammation research, 47(11), 421-427. (Year: 1998).*
Misra, G. S., & Subramanian, P. M. (1980). Three new flavone glycosides from Vitex negundo. Planta Medica, 38(02), 155-160. (Year: 1980).*
Wu, Hong-Lin, Yuan-Feng Tong, and Song Wu. 2014. "A Convenient Semisynthesis of Myricetin-3-O-β-d -Glucuronide." Journal of Asian Natural Products Research 16 (5): 522-26. (Year: 2014).*
Schramm et al. DE 4034586 A1, 1992, as translated by espacenet on May 18, 2020 (Year: 1992).*
First Chinese Office Action issued in Chinese patent application No. 201710658738.0, dated Apr. 16, 2019.
Second Chinese Office Action issued in Chinese patent application No. 201710658738.0, dated Oct. 16, 2019.
Power, K. et al., "Purified rutin and rutin-rich asparagus attenuates disease severity and tissue damage following dextran sodium sulfate-induced colitis," Mol. Nutr. Food Res. 2016, vol. 60, pp. 2396-2412.

(Continued)

*Primary Examiner* — Dale R Miller
(74) *Attorney, Agent, or Firm* — Faegre Drinker Biddle & Reath LLP

(57) ABSTRACT

The present invention provides a myricetin derivative, a preparation method thereof, a pharmaceutical composition containing the same, an application thereof for treating colitis, preventing and treating colitis-associated tumorigenesis and treating colorectal cancer, and an application thereof in preparing a composition for modulating activities of endoplasmic reticulum stress signaling molecules. The myricetin derivative disclosed herein has excellent water solubility, and has biological activities including inhibition of colitis, prevention and treatment of colitis-associated tumorigenesis, and treatment of colorectal cancer. The preparation method disclosed herein uses myricetrin as starting material which is economical and easily available. With the merits of low cost, high yield, high product purity and suitability for large-scale industrial production, the preparation method disclosed herein represents significant market value and economic prospects.

14 Claims, 7 Drawing Sheets

(56) References Cited

OTHER PUBLICATIONS

Truchado, P. et al., "Liquid chromatography-tandem mass spectrometry reveals the widespread occurrence of flavonoid glycosides in honey, and their potential as floral origin markers," Journal of Chromatography A., vol. 1216, Aug. 3, 2009, pp. 7241-7248.

Zhang, Y. et al., "Antioxidative flavonol glycosides from the flowers of *Abelmouschus manihot*" J. Nat. Med., vol. 67, Mar. 10, 2012, pp. 78-85.

Van, N.T.H. et al., "Chemical components from the leaves of *Ardisia insularis* and their cytotoxic activity," Arch. Pharm. Res., vol. 38, Mar. 21, 2015, pp. 1926-1931.

Yim, S.H. et al., "Phenolic Constituents from the Flowers of *Hamamelis japonica* Sieb. et Zucc.," Natural Product Sciences, 21(3), Dec. 31, 2015, pp. 162-169.

Schwanke, R.C. et al., "Oral administration of the flavonoid myricitrin prevents dextran sulfate sodium-induced experimental colitis in mice through modulation of PI3K/Akt signaling pathway," Mol. Nutr. Food Res., vol. 57, Dec. 31, 2013, pp. 1938-1949.

Lu, Cai-ling et al., "Effect of myricetin on the proliferation of human colorectal cancer cell line RKO," Journal of Reproductive Medicine, vol. 17(4), Aug. 31, 2008, pp. 291-293.

Wu, Shaohua et al., "Myricetin Induces Apoptosis in Endoplasmic Reticulum Stress Pathway and DNA Fragmentation Method of Ovarian Cancer SKOV3 Cells," Medical Journal of Chinese People's Health, vol. 27, Bimonthly Issue 14, Jul. 31, 2015, p. 169.

Harikant, P. M. et al., "Chemical Examination of Leucaena Leucocephala," Acta Ciencia Indica, vol. XXXIV p. No. 3, 252 (2008).

Li, Chun-mei, et al., "Isolation and identification of chemical constituents of flowers of Abelmoschus manihot (L.) Medic. Flos (I)," Journal of Shyenyang Pharmaceutical University, vol. 27, No. 9, Sep. 30, 2010, pp. 711-713.

Yadava, R. N. et al., "A novel bioactive flavonol glycoside from *Teramnus labialis* Spreng," Natural Product Research, vol. 18, No. 6, Dec. 2004, pp. 537-542.

Mizuno, Mizuo, et al., "Four Flavonol Glycosides from *Achlys Triphylla*," Phytochemistry, vol. 31, No. 1, Dec. 31, 1992, pp. 301-303.

Zhao, J. P. et al., Phytochemical Investigation of *Turnera diffusa*, J. Nat. Prod., vol. 70, Jul. 2, 2007, pp. 289-292.

Terzić, J. et al., "Inflammation and Colon Cancer," Gastroenterology 2010, vol. 138, pp. 2101-2114.

Extended European search report issued in European patent application No. 17838641.3, dated May 27, 2020.

Park, Kwang-Su et al., "Myricetin: biological activity related to human health," Applied Biological Chemistry, The Korean Society for Applied Biological Chemistry, Seoul, vol. 59, No. 2, Feb. 1, 2016, pp. 259-269.

\* cited by examiner

MYRICETIN DERIVATIVE AND PREPARING METHOD THEREOF, AND APPLICATION OF SAME FOR TREATING COLITIS, PREVENTING AND TREATING COLITIS TUMORIGENESIS, AND TREATING COLORECTAL CANCER

CROSS REFERENCE TO RELATED APPLICATIONS

This application is a National Stage of International Application No. PCT/CN2017/095925 filed Aug. 4, 2017, which claims benefit of Chinese Patent Application No. 201610665566.5 filed Aug. 12, 2016, both of which are herein incorporated by reference in their entirety.

TECHNICAL FIELD

The present invention relates to the field of medicine. More specifically, the present invention relates to a myricetin derivative, a method of preparing a myricetin derivative and an application of a myricetin derivative for preparing a drug intended for treating colitis, preventing and treating colitis-associated tumorigenesis and treating colorectal cancer.

BACKGROUND ART

Colitis refers to inflammatory lesions of the colon induced by various causes, and its main clinical symptoms include recurring bloody diarrhea with/without mucus or pus in the stools, abdominal pain, rectal tenesmus, constipation, weight loss and fatigue. Chronic colitis, including ulcerative colitis (UC), granulomatous colitis and Crohn's disease, is the main precancerous lesion leading to colorectal cancer (CRC). CRC is one of the most common malignant tumors seen in the clinic. The incidence and mortality of CRC ranks third and fourth respectively among those of malignant tumors. The cause of CRC is currently unclear, and clinically CRC is known to be associated with the followings: (1) intestinal adenoma or polyposis, accounting for more than half of the incidence of colon cancer; (2) inflammatory bowel disease, including chronic UC, granulomatous colitis; (3) tumor microenvironmental factors, such as high-fat diet and biotoxin stimulation, which accelerate the conversion from signaling cascades associated with inflammation to those associated with cancer. Pathological anomalies, such as chronic inflammation, hyperplasia, polyps, multiple adenomas and cancer, can be seen in different developmental stages of CRC.

Effects of drug treatment for colorectal cancer is not obvious. Early detection and treatment are currently the best prevention and treatment practices for CRC. One of the best strategies is to find economical and effective prophylactic drugs without significant toxicity. Non-steroidal anti-inflammatory drugs are the major type of drugs for CRC prevention. Currently Aspirin alone or together with calcium, vitamin D or folic acid is the most widely used regime for CRC prevention, yet the clinical application of aspirin is limited manly due to its adverse effects such as increased risk of bleeding and peptic ulcer. Other drugs such as corticosteroids and immunomodulators may also be applied, whereas the former has significant side effects, and the latter is very expensive.

3,5,7-trihydroxy-2-(3,4,5-trihydroxyphenyl)-4H-1-benzofuran-4-one, namely myricetin, is a compound of the flavonoid class. Myricetin is the main chemical component in leaves, skin and roots of *Myrica rubra* in Myricaceae family. The present inventors studied the biological activities of myricetin in adenomatous polyposis *coli* (APC) gene mutation mouse model, and found that myricetin had strong inhibitory activities against colitis and colitis-associated tumorigenesis. Chemical analysis shows that myricetin itself has disadvantages such as poor water solubility, low stability and low bioavailability, unsuitable for further development. With structural modification, the present inventors not only increase water solubility but also significantly increase pharmacological activity and thereby draggability of a myricetin derivative, which is of great importance for treating colitis, preventing and treating colitis-associated tumorigenesis and treating colorectal cancer.

DESCRIPTION OF THE INVENTION

In view of the deficiencies of the prior art, the present invention provides a myricetin derivative and preparation method thereof; furthermore, the present invention also provides pharmaceutically acceptable salts thereof, an application thereof for treating colitis, preventing and treating colitis-associated tumorigenesis, and treating colorectal cancer. Pharmacological experiments indicate that the myricetin derivative disclosed herein has significant biological activities of inhibiting colitis, preventing and treating colitis-associated tumorigenesis, and treating colorectal cancer. In order to achieve the above-mentioned object of the invention, technical solutions of the present invention are provided as follows:

Technical Solutions of the Invention

A myricetin derivative having a structure of Formula (I):

(I)

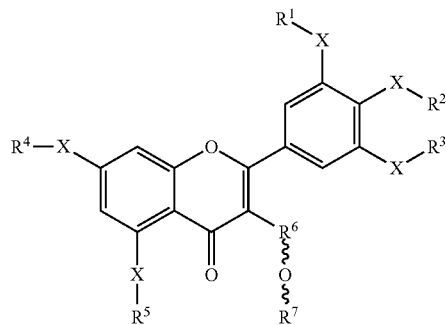

wherein:
X is selected from O, NH, S;
$R^1$, $R^2$, $R^3$, and $R^4$ are each selected from the group consisting of a hydrogen atom, a benzyl group, a substituted benzyl group, a C1-C24 alkyl group;
$R^5$=a hydrogen atom or a benzyl group;
$\} = -(CH)_n-$, wherein n=0-5;
$R^6$=tetrose (erythrose, threose); pentose (ribose, deoxyribose, arabinose, lyxose, xylose, etc); hexose (glucose, mannose, altrose, gulose, sorbose, talose, allose, galactose, idose, etc), or substituted monosaccharide derivatives thereof; $R^7$=tetrose (erythrose, threose); pentose (ribose, deoxyribose, arabinose, lyxose, xylose, etc); hexose (glucose, mannose, altrose, gulose, sorbose, talose, allose, galactose, idose, etc), or substituted monosaccharide derivatives thereof.

Further, said $R^6$ is selected from the group consisting of glucose, galactose, or substituted monosaccharide derivatives thereof.

Further, said $R^7$ is selected from the group consisting of galactose, ribose, mannose, or substituted monosaccharide derivatives thereof.

Further, said substitution refers to multi-substitution.

Further, preferably $R^6$ and $R^7$ are not galactose and galactose respectively, nor rhamnose and galactose respectively, nor xylose and glucose respectively, nor mannose and glucose respectively.

Further, the present invention also includes isomers, racemates, pharmaceutically acceptable salts, hydrates, prodrugs, derivatives or analogs of various compounds represented by said formula which also have similar pharmaceutical activities such as inhibitory activities against enteritis or intestinal cancer.

The term "isomers", as used herein, includes conformers, optical isomers (such as enantiomers and diastereomers), geometric isomers (such as cis-trans isomers).

The term "derivatives or analogs", as used herein, refers to compounds that have similar structures to, and particularly have the same core structure as, those represented by said formula, wherein compounds may remain similar pharmaceutical activities such as inhibitory activity against enteritis when some of their functional moieties are substituted by other similar moieties, for example, substitution between halogen moieties such as fluorine, chlorine, bromine and iodine, or substitution between OH, $OCH_3$ and $OCH_2CH_3$.

The term "pharmaceutically acceptable salts", as used herein, refers to salts formed by aforementioned compounds reacting with inorganic acids, organic acids, alkali metals or alkaline earth metals. These salts include, but are not limited to: (1) salts formed with the following inorganic acids: hydrochloric acid, hydrobromic acid, hydroiodic acid, sulfuric acid, nitric acid, phosphoric acid; (2) salts formed with the following organic acids: acetic acid, lactic acid, citric acid, succinic acid, fumaric acid, gluconic acid, benzoic acid, methanesulfonic acid, ethanesulfonic acid, benzenesulfonic acid, p-toluenesulfonic acid, oxalic acid, succinic acid, tartaric acid, maleic acid or arginine; (3) other salts, including salts formed with alkali metals or alkaline earth metals (such as sodium, potassium, calcium or magnesium), ammonium salts or water-soluble amine salts (such as N-methylglucamine salts), lower alkanol ammonium salts and other pharmaceutically acceptable amine salts (such as methylamine salts, ethylamine salts, propylamine salts, dimethylamine salts, trimethylamine salts, diethylamine salts, triethylamine salts, tert-butylamine salts, ethylenediamine salts, hydroxyethylamine salts, dihydroxyethylamine salts, trihydroxyethylamine salts, and amine salts formed with morpholine, piperazine or lysine), or other common forms of "prodrugs".

Compounds have one or more asymmetric centers, and therefore may exist as racemic mixtures, individual enantiomers, individual diastereomers, diastereomeric mixtures, cis- or trans-isomers.

The term "prodrugs", as used herein, refers to compounds that may be converted into a myricetin derivative represented by the formula disclosed herein via enzymatic or chemical reaction in patients after being administered appropriately, and pharmaceutically acceptable salts thereof or solution that contains the same. Said prodrugs include, but are not limited to, the following compounds: carboxylate esters, carbonate esters, phosphate esters, nitrate esters, sulfate esters, sulfone esters, sulfoxide esters, amides, carbamates, azo compounds, phosphamides, glucosides, ethers and acetals.

Further, said myricetin derivative of Formula (I) is specifically M2, M3, M5 (S1), M6 (S2), M6', M7 (S3), M8, M9, M10, M13 and M14, as shown below:

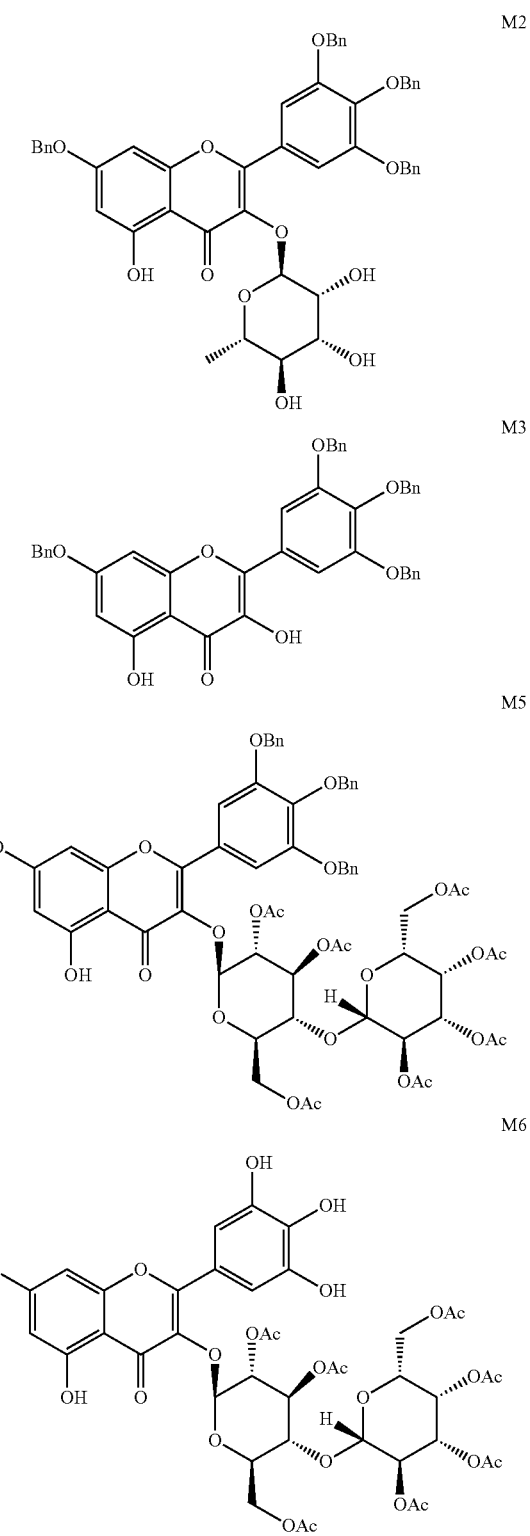

M6'
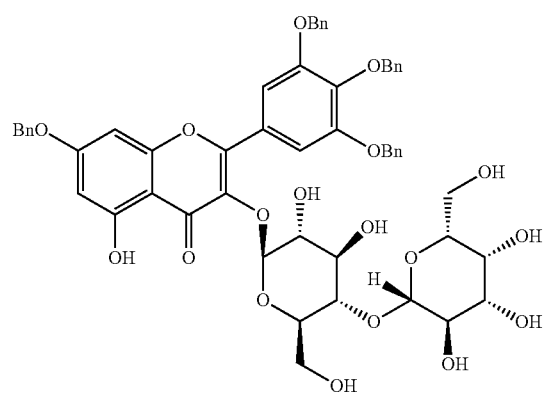
M9
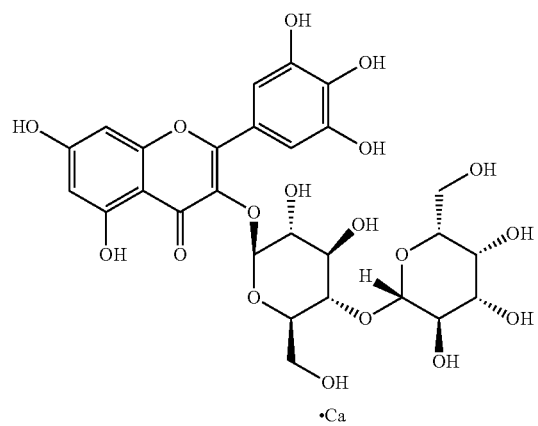
M7
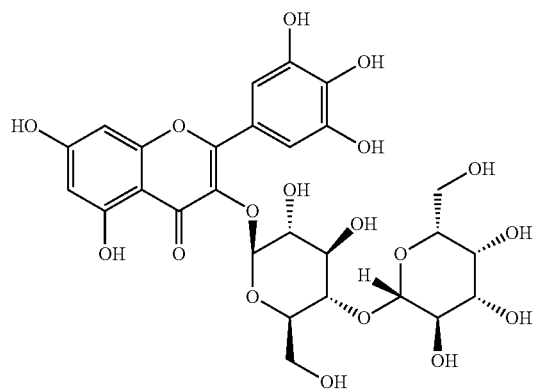
M10
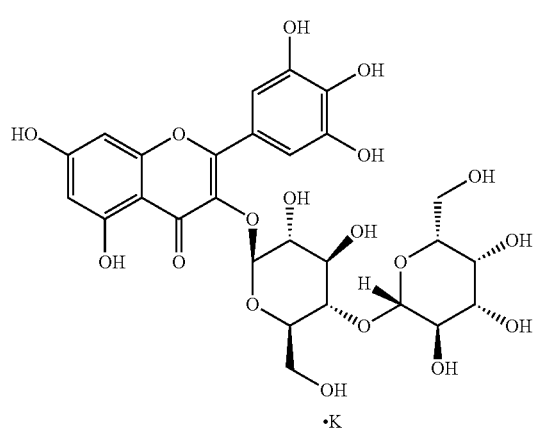
M8
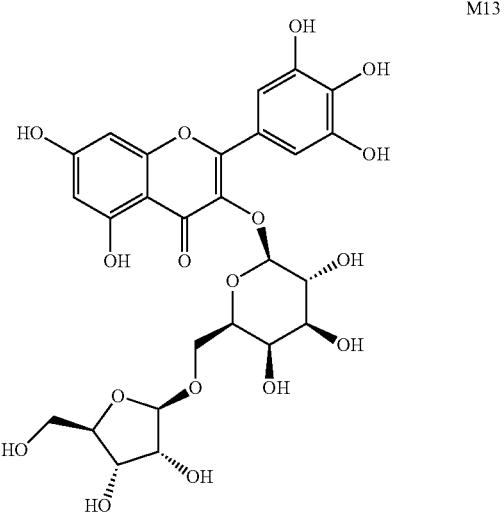
M13

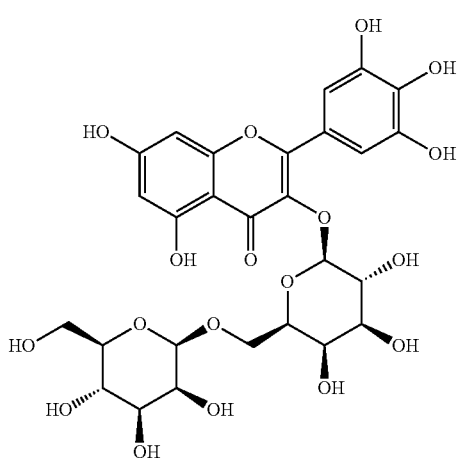

M14

The present invention also provides a method of preparing the myricetin derivative disclosed herein, comprising:
(1) protecting phenolic hydroxyl groups at the C-7, C-3', C-4' and C-5' positions of the starting material myricetrin, to form benzyl-protected myricetrin derivative M2 which is represented by the following formula:

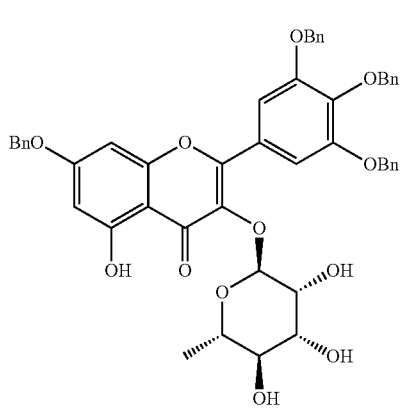

M2

(2) removing the C-3 rhamnose from M2 to form benzyl-protected myricetin derivative M3 which is represented by the following formula:

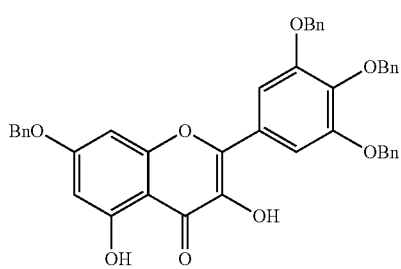

M3

(3) condensing the benzyl-protected myricetin derivative M3 with various acetyl-protected glycosyl bromides in the presence of an alkali to form various acetyl-protected glycosyl derivative M5X represented by Formula (III) as shown below, wherein $R^6$ and $R^7$ are different monosaccharides and n=1, 2, 3, 4, 5 or 6;

(III)

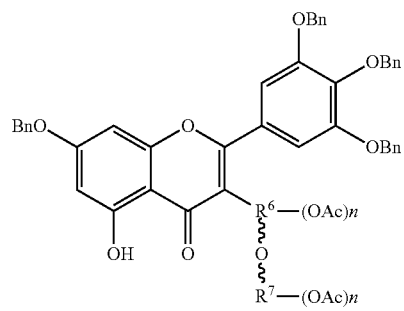

M5X (4) deprotecting the benzyl group from M5X by palladium-carbon catalysis to obtain various acetyl-protected glycosyl derivative M6X; or deprotecting the acetyl group from M5X in the presence of sodium methoxide to obtain various benzyl-protected glycosyl derivative M6'X represented by Formula (IV) and (V) respectively as shown below, wherein $R^6$ and $R^7$ are different monosaccharides and n=1, 2, 3, 4, 5 or 6:

(IV)

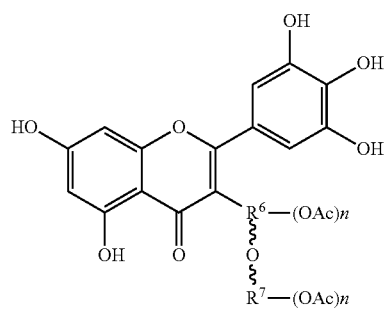

M6X (V)

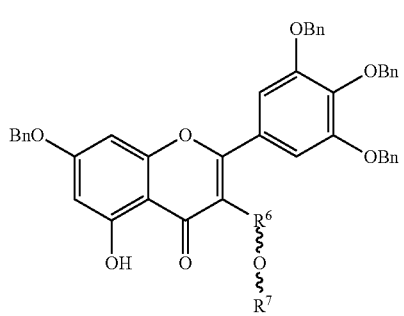

M6'X (5) deprotecting the acetyl group from M6X in the presence of sodium methoxide to obtain various glycosyl derivative M7X; or deprotecting the benzyl group from M6'X by palladium-carbon catalysis to obtain M7X; wherein said M7X refers to compounds represented by Formula (VI) as shown below, wherein $R^6$ and $R^7$ are different monosaccharides:

(VI)

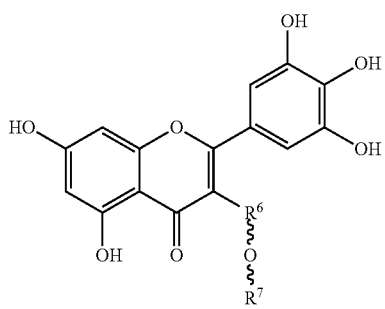
M7X (6) myricetin derivative M7X reacting with potassium hydroxide to obtain myricetin derivative M8X represented by the following formula, wherein $R^6$ and $R^7$ are different monosaccharides;

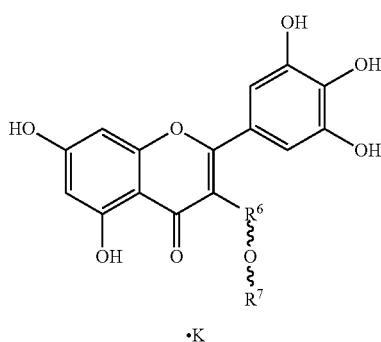
M8X
·K (7) myricetin derivative M7X reacting with calcium hydroxide to obtain myricetin derivative M9X represented by the following formula, wherein $R^6$ and $R^7$ are different monosaccharides;

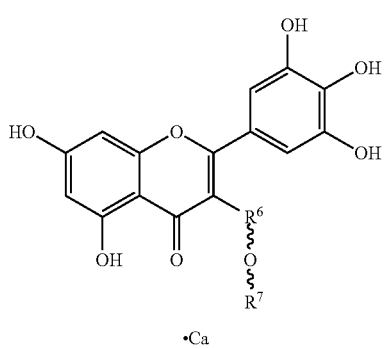
M9X
·Ca (8) myricetin derivative M7X reacting with sodium hydroxide to obtain myricetin derivative M10X represented by the following formula, wherein $R^6$ and $R^7$ are different monosaccharides;

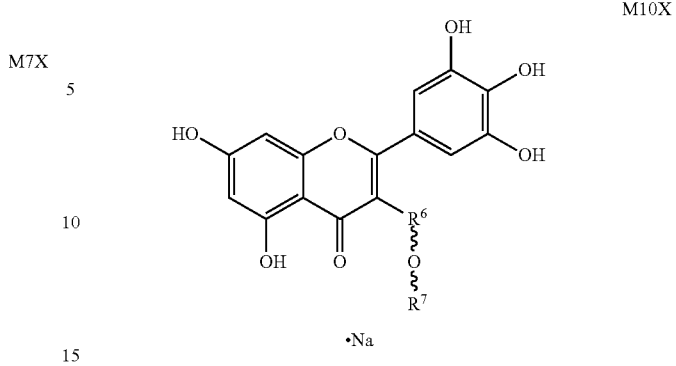
M10X
·Na

Further: said alkali is selected from the group consisting of potassium carbonate, sodium carbonate, cesium carbonate, triethylamine, diisopropylethylamine or 4-dimethylaminopyridine, or their combination.

Further: said alkali refers to potassium carbonate.

The present invention also provides an application of the myricetin derivative disclosed herein for treating colitis, preventing and treating colitis-associated tumorigenesis and treating colorectal cancer.

The term "colitis", as used herein, refers to inflammatory lesions of the colon induced by various causes, and its main clinical symptoms include recurring bloody diarrhea with/without mucus or pus in the stools, abdominal pain, rectal tenesmus, constipation, weight loss and fatigue.

The term "colitis-associated tumorigenesis", as used herein, refers to a high correlation between chronic colitis, a major precancerous lesion leading to colorectal cancer, and intestinal adenoma or colon cancer. More than 20% of the patients with inflammatory bowel disease will develop colon cancer within 30 years since the time of diagnosis. Different developmental stages, such as chronic inflammation, hyperplasia, polyps, multiple adenomas and carcinogenesis can be verified via pathological analysis.

The term "colorectal cancer", as used herein, refers to one of the most common malignant tumors in the clinic, ranking third in incidence and fourth in mortality among all malignant tumors. The cause of colorectal cancer is currently unclear. Although the treatment for inflammatory bowel disease is normally accompanied by good prognosis, once carcinogenesis occurred, the cancer tissue usually disseminates fast and results in poor prognosis. Therefore, in recent years, prophylactic treatment is advocated for chronic colitis-associated tumorigenesis. Further, the myricetin derivative disclosed herein is represented by Formula (I):

(I)

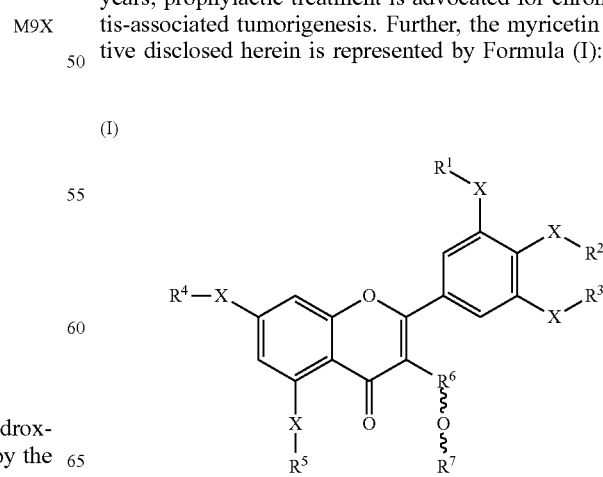

wherein:

X is selected from O, NH, S;

$R^1$, $R^2$, $R^3$ and $R^4$ are each selected from a hydrogen atom, a benzyl group, a substituted benzyl group, a C1-C24 alkyl group;

$R^5$=a hydrogen atom or a benzyl group;

$R^6$=monosaccharides or substituted derivatives thereof;

$R^7$=monosaccharides or substituted derivatives thereof.

Further, $R^6$=tetrose (erythrose, threose); pentose (ribose, deoxyribose, arabinose, lyxose, xylose, etc); hexose (glucose, mannose, altrose, gulose, sorbose, talose, allose, galactose, idose, etc) or substituted monosaccharide derivatives thereof.

Further, $R^7$=tetrose (erythrose, threose); pentose (ribose, deoxyribose, arabinose, lyxose, xylose, etc); hexose (glucose, mannose, altrose, gulose, sorbose, talose, allose, galactose, idose, etc) or substituted monosaccharide derivatives thereof.

Further, $R^6$ is selected from the group consisting of glucose, ribose, deoxyribose, xylose, arabinose, mannose, altrose, gulose, sorbose, tagatose, erythrose, allose, threose, lyxose, idose, galactose or substituted monosaccharide derivatives thereof; $R^7$ is selected from the group consisting of galactose, ribose, mannose or substituted monosaccharide derivatives thereof.

The term "monosaccharides", as used herein, refers to the basic unit constituting various glycosyl molecules. Naturally-occurring monosaccharides are generally D-form. Monosaccharides can exist either in a cyclic form or in an open chain form.

Further, $R^6$ is selected from the group consisting of glucose, galactose or substituted monosaccharide derivatives thereof.

Further, said substitution refers to multi-substitution.

Further, the myricetin derivative disclosed herein is:

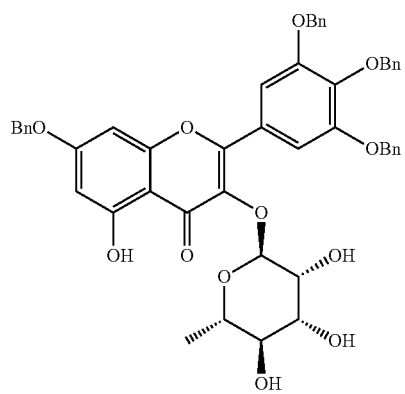

M2

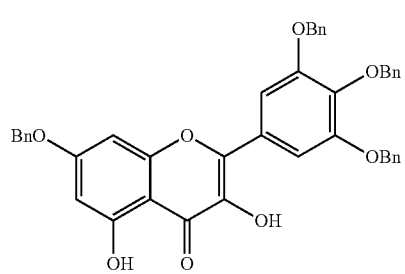

M3

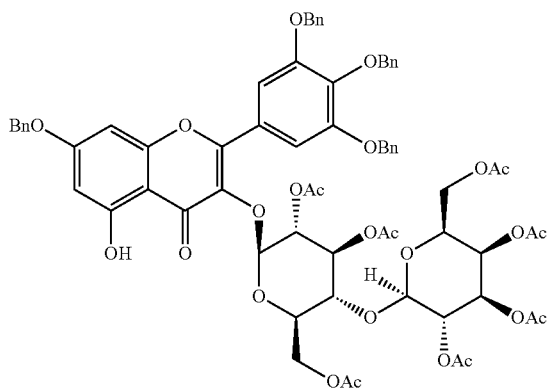

M5

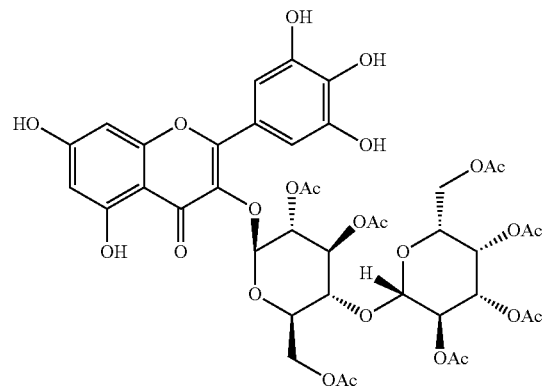

M6

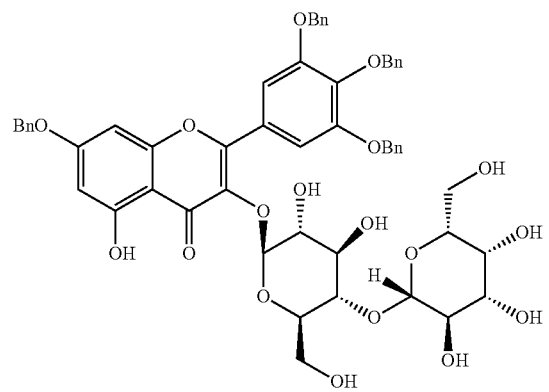

M6'

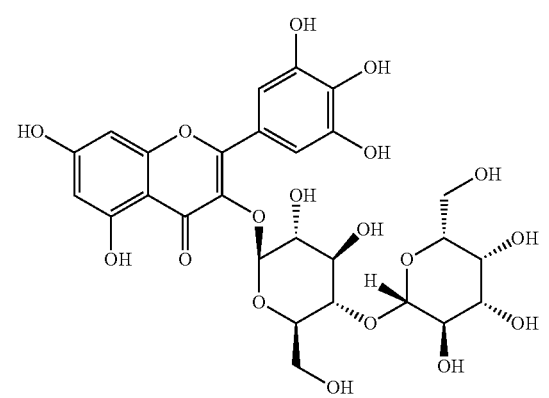

M7

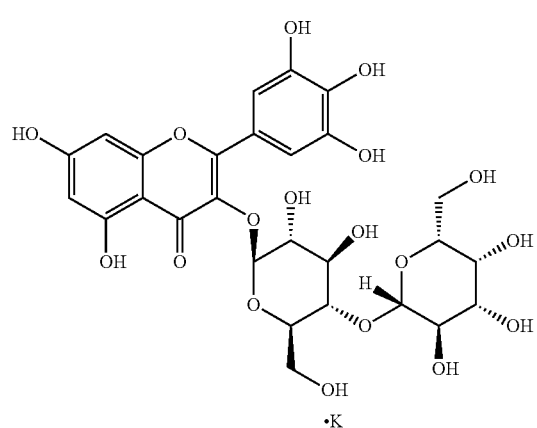
M8
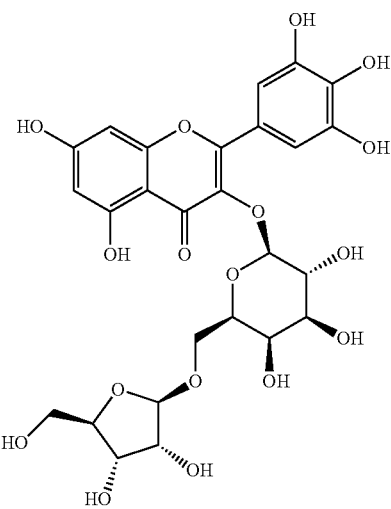
M13
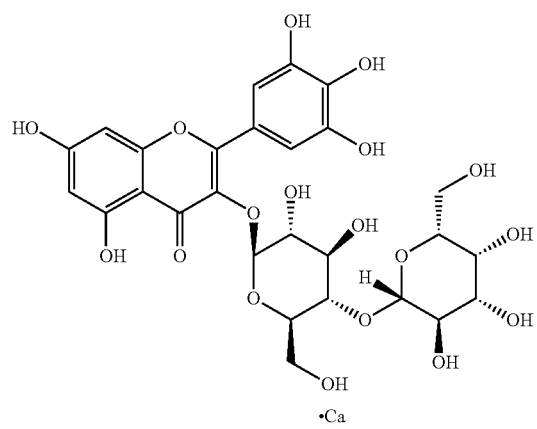
M9
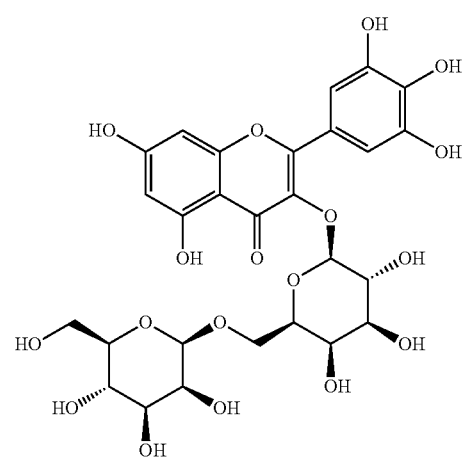
M14
Further, the myricetin derivative disclosed herein is:
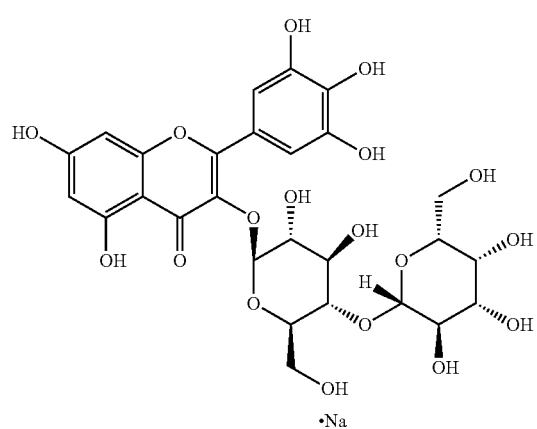
M10
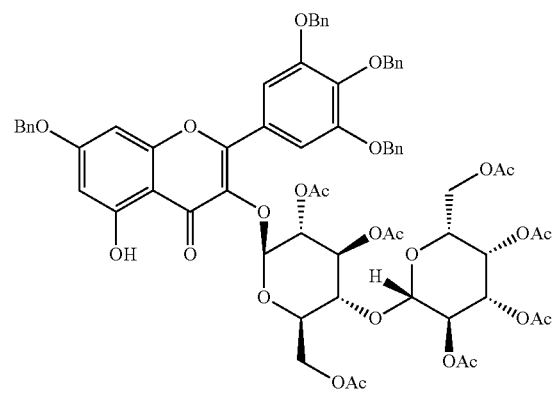
M5

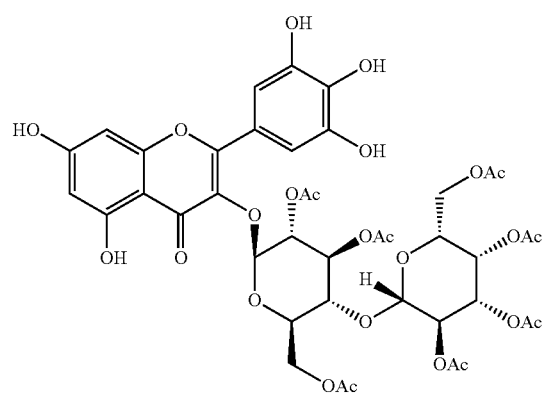
M6
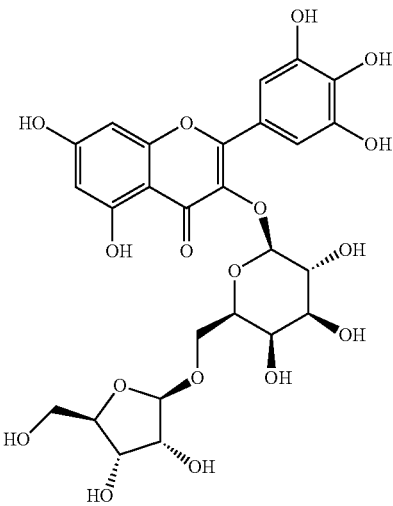
M13
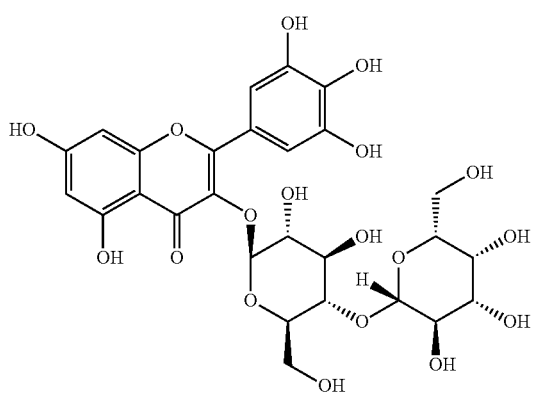
M7
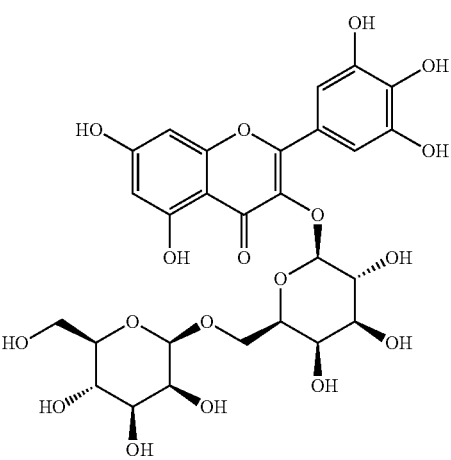
M14
Further, said colitis comprises chronic colitis and acute colitis.
The present invention also provides an application of a myricetin derivative for preparing a composition for modulating the activity of endoplasmic reticulum stress signaling molecules.
Further, the myricetin derivative disclosed herein is represented by Formula (I):
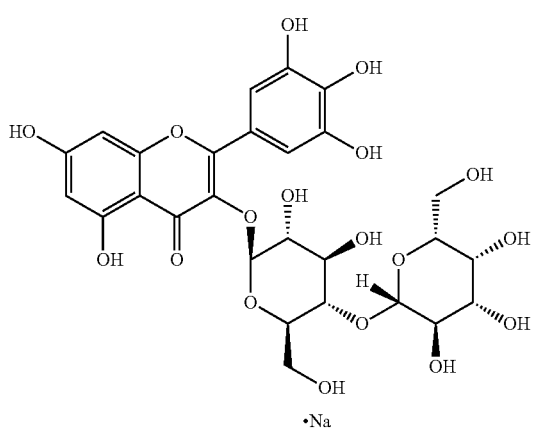
M10
·Na
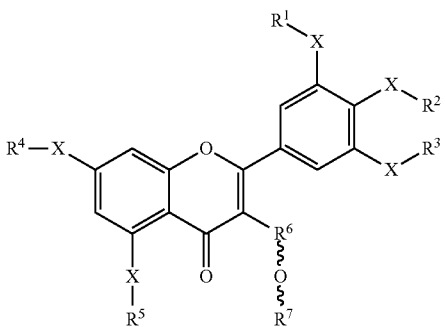
(I)

wherein:

X is selected from O, NH, S;

$R^1$, $R^2$, $R^3$ and $R^4$ are each selected from a hydrogen atom, a benzyl group, a substituted benzyl group, a C1-C24 alkyl group;

$R^5$=a hydrogen atom or a benzyl group;

⸺$(CH)_n$⸺, where n=0-5;

$R^6$=monosaccharides or substituted derivatives thereof;

$R^7$=monosaccharides or substituted derivatives thereof.

Further, $R^6$ is selected from the group consisting of glucose, ribose, deoxyribose, xylose, arabinose, mannose, altrose, gulose, sorbose, tagatose, erythrose, allose, threose, lyxose, idose, galactose or substituted monosaccharide derivatives thereof.

Further, $R^7$ is selected from the group consisting of galactose, ribose, mannose or substituted monosaccharide derivatives thereof.

Further, $R^6$ is selected from the group consisting of glucose, galactose or substituted monosaccharide derivatives thereof.

Further, the myricetin derivative disclosed herein is:

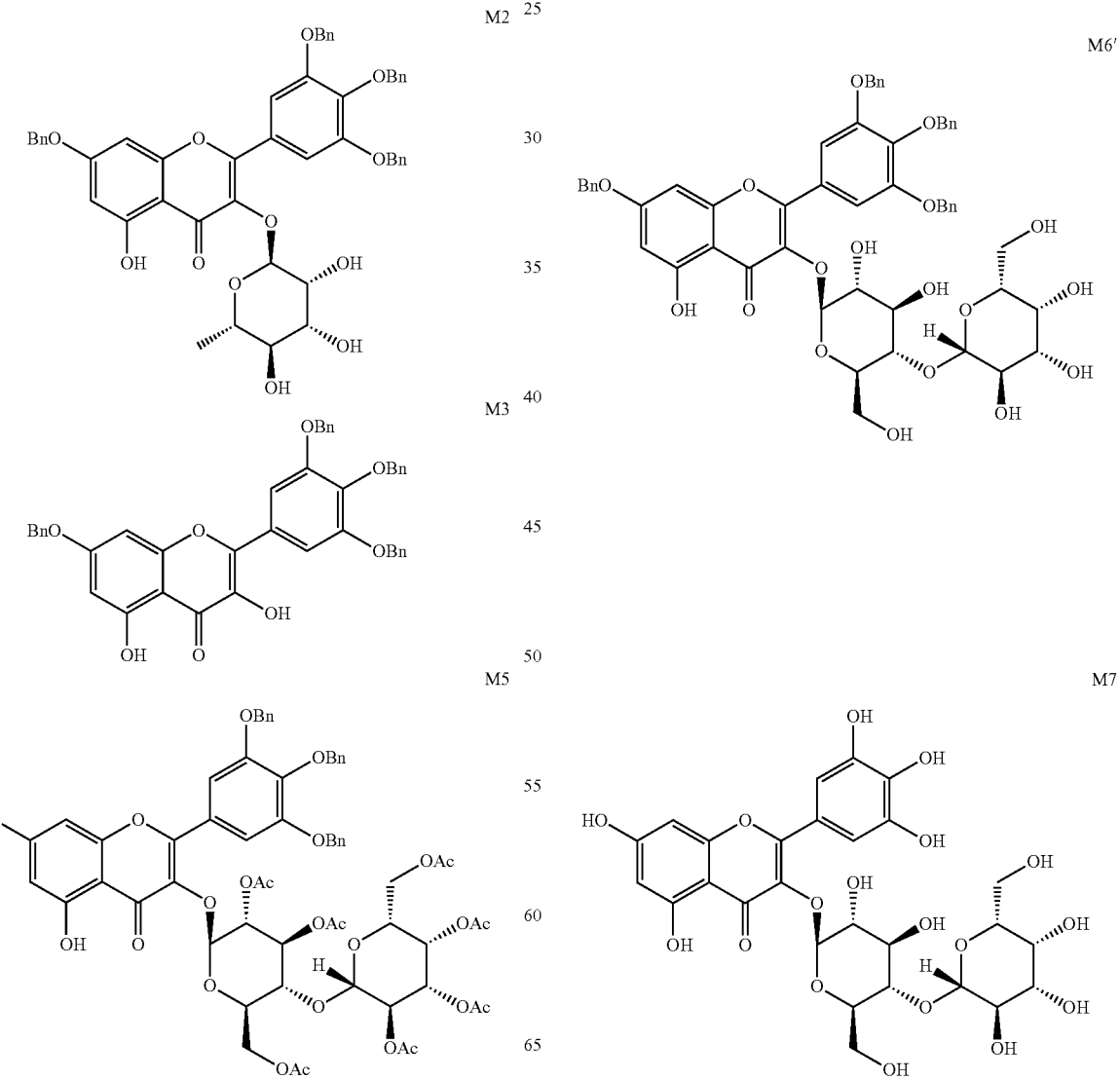

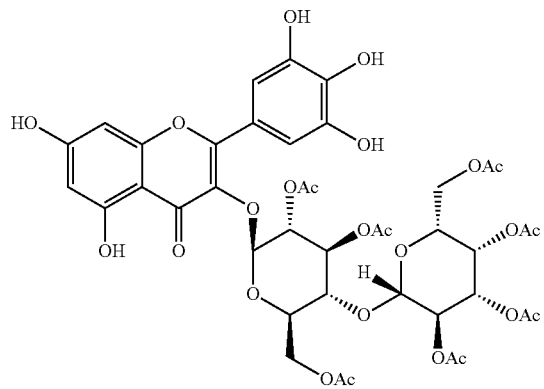

M8
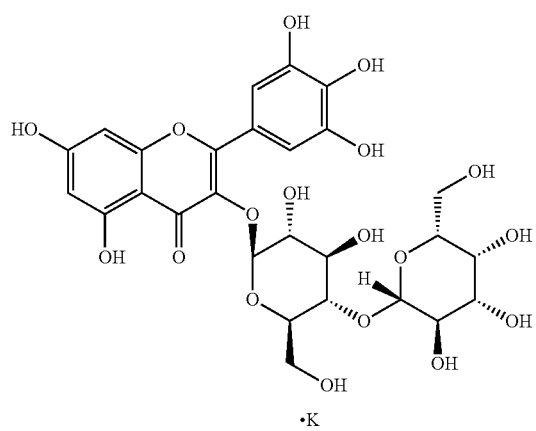
·K
M9
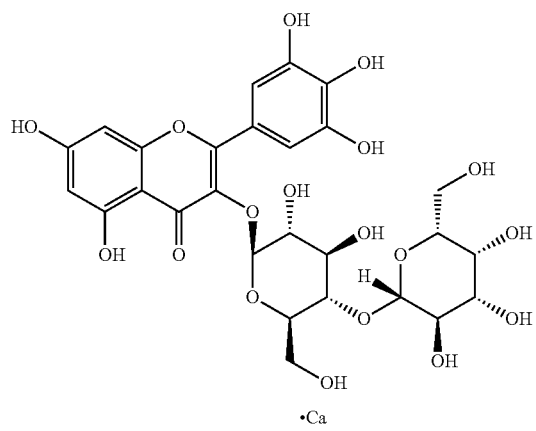
·Ca
M10
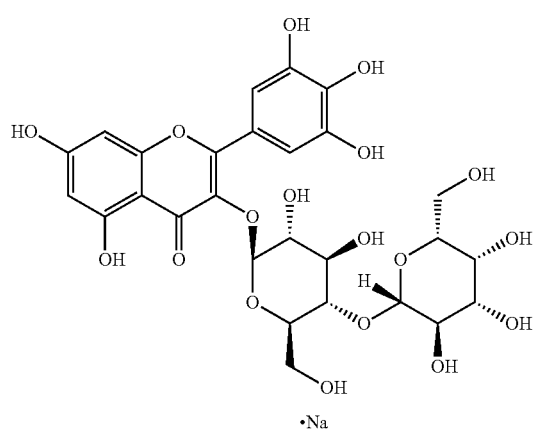
·Na
M13
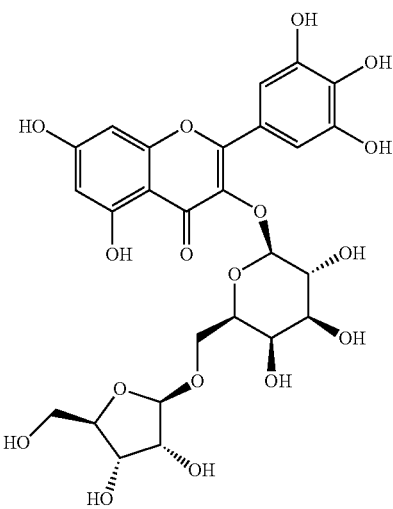
M14
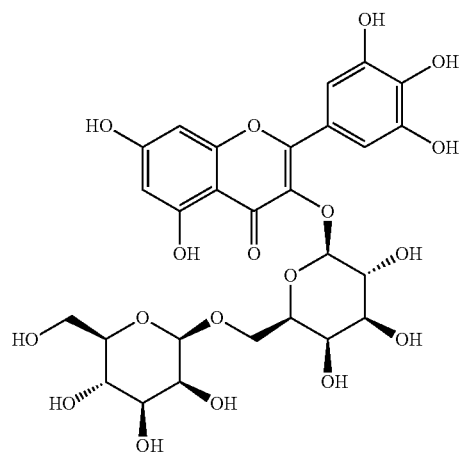
Further, the myricetin derivative disclosed herein is:
M5
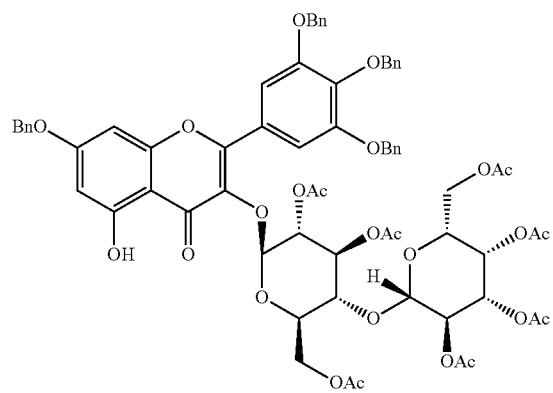

-continued

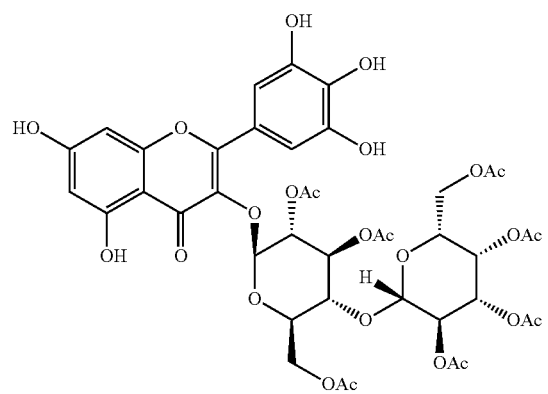
M6

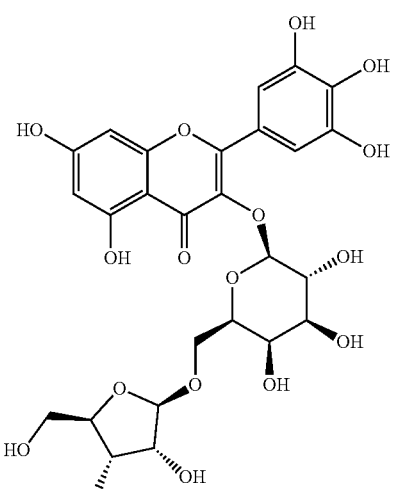
M13

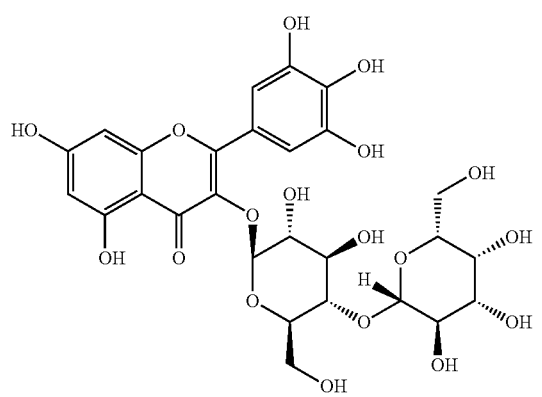
M7

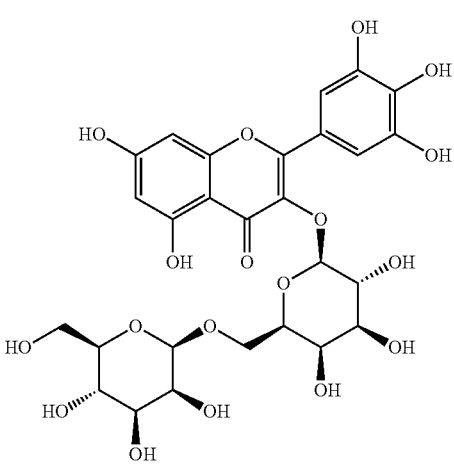
M14

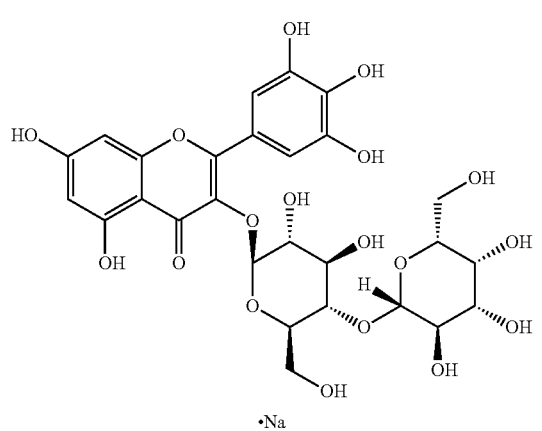
M10

Further, said endoplasmic reticulum stress signaling molecules comprise GRP78, ATF6, P-eIF-2α, IREα, ATG3, ATG5, ATG7, ATG12, ATG16l1.

Further, said composition is used for treating diseases associated with endoplasmic reticulum stress.

The term "endoplasmic reticulum stress", as used herein, refers to a condition where, in the case of hypoxia, oxidative stress, abnormal glycosylation reaction and imbalance of calcium ion homeostasis, the amount of unfolded endoplasmic reticulum protein significantly increases to the extent that it exceeds the processing capacity of endoplasmic reticulum, resulting in activation of a number of related cellular signaling cascades to cope with such intracellular changes and restore protein folding environment back to normal in the endoplasmic reticulum. The endoplasmic reticulum stress induced by AOM/DSS is mainly characterized by swelling of the endoplasmic reticulum membrane, irregular arrangement of fractures, increased expression of signaling molecules including GRP78, ATF6, P-eIF-2a and IREa, and cellular autophagy, which involves formation of autophagic vacuoles in colonic epithelial cells, mitochondrial swelling, and up-regulation of signaling molecules ATG3, ATG5, ATG7, ATG12 and ATG16l1, further resulting in up-regulation of autophagosomes.

Further, said diseases associated with endoplasmic reticulum stress refer to colitis and colorectal cancer.

The present invention provides a pharmaceutical composition comprising a compound of Formula (I), or its pharmaceutically acceptable salt, and a pharmaceutically acceptable carrier.

Said pharmaceutically acceptable carrier refers to an alkaline adjuvant or solvent that has certain solubilizing effect, wherein said alkaline adjuvant is selected from the group consisting of sodium bicarbonate, potassium bicarbonate, sodium carbonate, sodium hydroxide, potassium hydroxide, sodium acetate, sodium octoate, sodium iso-octanoate, sodium citrate, sodium tartrate, or their combination; wherein said alkaline solvent is selected from the group consisting of sodium bicarbonate solution or sodium bicarbonate injection, sodium citrate solution or sodium citrate injection, sodium lactate solution or sodium lactate injection, compound sodium lactate-glucose solution or compound sodium lactate-glucose injection, sodium oxybate solution or sodium oxybate injection, sodium glutamate solution or sodium glutamate injection, potassium glutamate solution or potassium glutamate injection, or their combination.

Wherein the alkaline adjuvant in said pharmaceutical composition is preferably sodium bicarbonate or potassium bicarbonate or sodium hydroxide, and the alkaline solvent in said pharmaceutical composition is preferably sodium bicarbonate solution or sodium bicarbonate injection.

The beneficial effects of the present invention:
(1) The present invention provides a myricetin derivative of Formula (I); data shows that the myricetin derivative provided by the present invention has excellent water solubility, and has pharmaceutical activities of treating colitis, preventing and treating colitis-associated tumorigenesis, and treating colorectal cancer; the present invention also provides an application of the myricetin derivative disclosed herein for treating colitis, preventing and treating colitis-associated tumorigenesis, and treating colorectal cancer.
(2) The present invention provides a method of preparing a myricetin derivative, which utilizes myricetrin, an economical and easily available compound, as the starting material. With the merits of low cost, high yield, high product purity and suitability for large-scale industrial production, the preparation method disclosed herein represents significant market value and economic prospects.

DETAILED DESCRIPTION OF EMBODIMENTS

Figure 1:
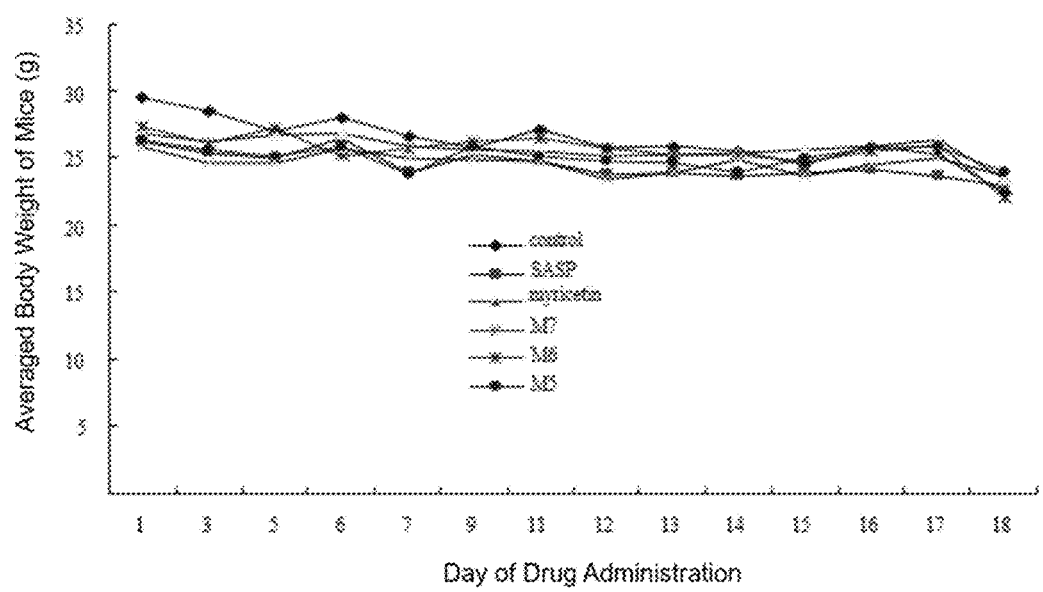
FIG. 1 illustrates the changes in body weight of each group of mice during drug administration in Example 8.

The invention will be further explained below in combination with the following examples.

Example 1

The synthetic route of myricetrin derivative M2 is as follows:

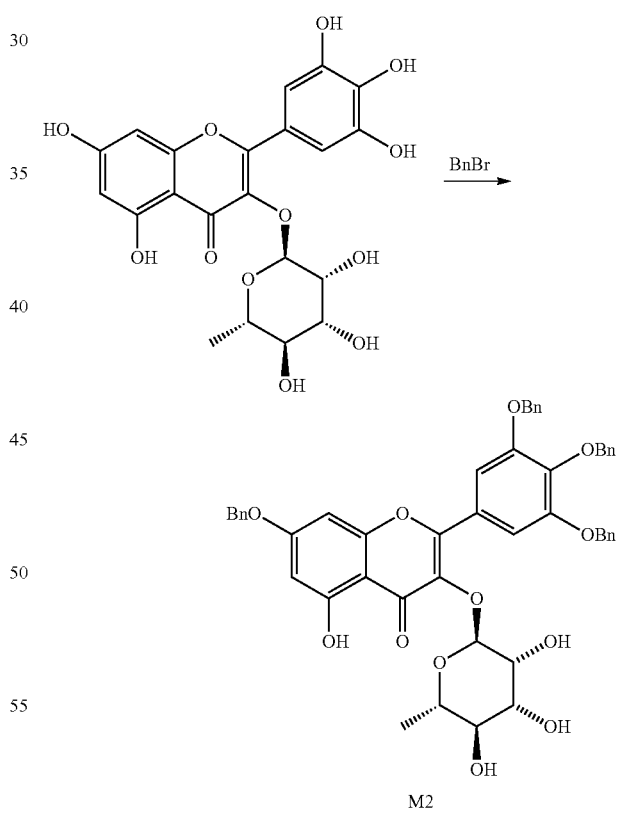

Myricetrin (100 g, 0.22 mol) was dissolved in N, N-dimethylformamide (1 L). Potassium carbonate (300 g, 2.16 mol) was then added. The mixture reacted at room temperature for 2 hours, added dropwise with benzyl bromide (370 g, 12.16 mol) and then heated to 80° C. for 60 hours. Upon completion of the reaction, the mixture was cooled to room temperature and added with 3 L of water. A solid was precipitated with stirring and filtrated. The resulting solid was then added with a 1:1 mixture of water and dichloromethane (3 L), and the pH was adjusted to be acidic with 2N hydrochloric acid. The organic phase was separated, and the aqueous phase was extracted three times with dichloromethane. The organic phases were combined, dried and concentrated to obtain 200 g of M2, which was used directly for the next step without purification.

Example 2

The synthetic route of myricetin derivative M3 is as follows:

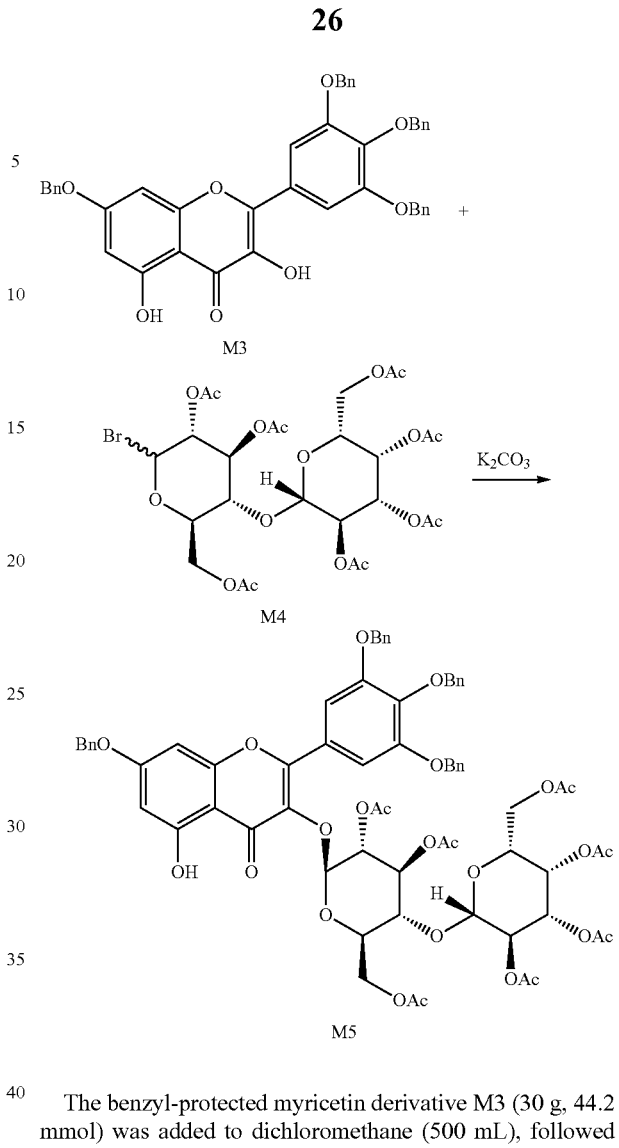

M2 (200 g) obtained in Example 1 was dissolved in tetrahydrofuran (1 L). 3N hydrochloric acid (1 L) was then added. The reaction mixture was heated under reflux for 12 hours, then cooled to room temperature. A solid was precipitated and filtered. The resulting solid was then added into a 1:1 mixture of ethanol/dichloromethane (0.8 L), heated under reflux and pulpified for 4 hours, cooled to room temperature and filtered to obtain 67 g of M3 as a yellowish solid with 45% yield.

1H NMR (500 MHz, DMSO-d6) δ=12.35 (s, 1H), 9.85 (s, 1H), 7.67 (s, 2H), 7.50 (t, J=6.7 Hz, 6H), 7.39 (m, 12H), 7.29 (d, J=1.5 Hz, 2H), 6.90 (d, J=2.2 Hz, 1H), 6.48 (d, J=2.2 Hz, 1H), 5.26 (s, 2H), 5.20 (s, 4H), 5.05 (s, 2H) ppm. ESI-MS: (m/z, %)=677 [M−H]−.

Example 3

The synthetic route of myricetin derivative M5 is as follows:

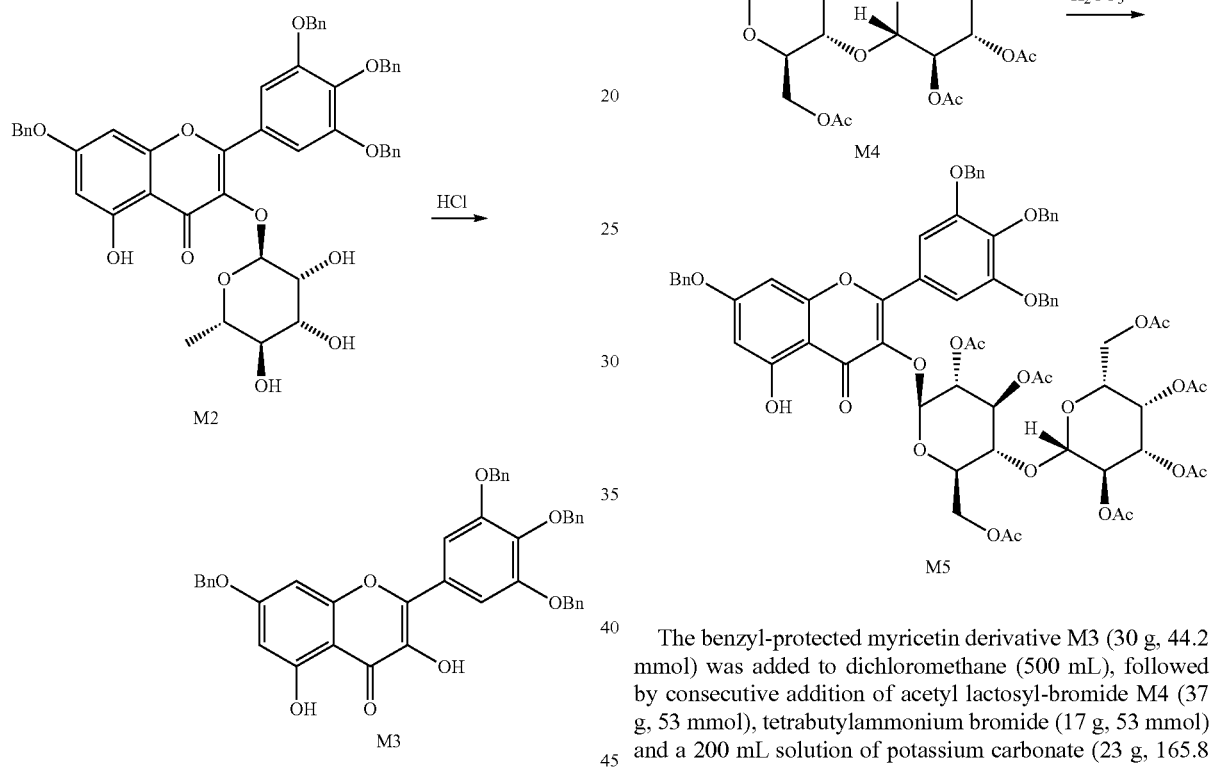

The benzyl-protected myricetin derivative M3 (30 g, 44.2 mmol) was added to dichloromethane (500 mL), followed by consecutive addition of acetyl lactosyl-bromide M4 (37 g, 53 mmol), tetrabutylammonium bromide (17 g, 53 mmol) and a 200 mL solution of potassium carbonate (23 g, 165.8 mmol). The reaction mixture was heated to 45° C. and stirred for 3 hours, and then water was added for phase separation. The organic phase was washed with water and brine consecutively and dried. 23 g of M5 as a yellow solid was obtained via column chromatography with 52% yield.

$^1$H NMR (500 MHz, CD$_3$C1) δ=12.43 (s, 1H), 7.52 (d, J=7.3 Hz, 4H), 7.49-7.33 (m, 15H), 7.30 (dd, J=4.9, 1.7 Hz, 3H), 6.48 (d, J=2.2 Hz, 1H), 6.45 (d, J=2.2 Hz, 1H), 5.56 (d, J=8 Hz, 1H), 5.33 (d, J=2.8 Hz, 1H), 5.24 (m, 5H), 5.16 (d, J=5.8 Hz, 4H), 5.12-5.05 (m, 2H), 4.92 (dd, J=10.4, 3.4 Hz, 1H), 4.41 (d, J=7.9 Hz, 1H), 4.35 (dd, J=12.0, 1.9 Hz, 1H), 4.08 (d, J=6.9 Hz, 2H), 3.90 (dd, J=12.0, 4.3 Hz, 1H), 3.83 (t, J=6.9 Hz, 1H), 3.74 (t, J=9.5 Hz, 1H), 3.60-3.48 (m, 1H), 2.15 (s, 3H), 2.08 (s, 3H), 2.06 (s, 3H), 2.01 (s, 3H), 1.98 (s, 3H), 1.95 (s, 3H), 1.82 (s, 3H) ppm. $^{13}$C NMR (125 MHz, CD$_3$C1) δ=177.47, 170.27, 170.15, 170.05 (2C), 169.89, 169.50, 168.87, 164.68, 161.98, 157.20, 156.64, 152.36 (2C), 140.76, 137.57, 136.96 (2C), 135.63, 134.00, 128.76 (2C), 128.55 (4C), 128.43 (2C), 128.23 (2C), 127.96 (2C), 127.94 (2C), 127.49 (4C), 127.44 (2C), 125.41, 108.99 (2C), 105.96, 100.97, 98.85, 98.74, 93.19, 76.02, 75.23, 72.78, 72.56, 71.96, 71.25 (2C), 70.95, 70.70, 70.50, 68.98, 66.57, 61.02, 60.79, 20.81, 20.79, 20.62, 20.57, 20.56, 20.49, 20.39 ppm.

Example 4

The synthetic route of myricetin derivative M6 is as follows:

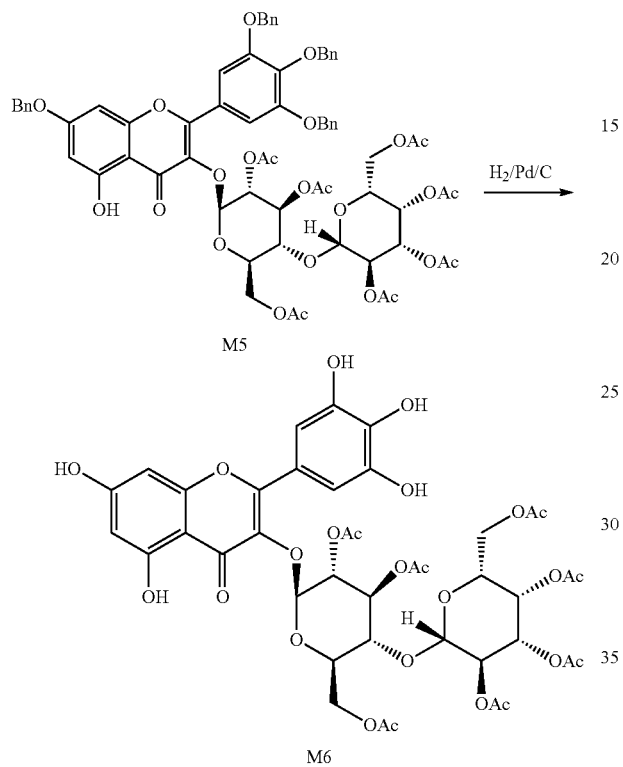

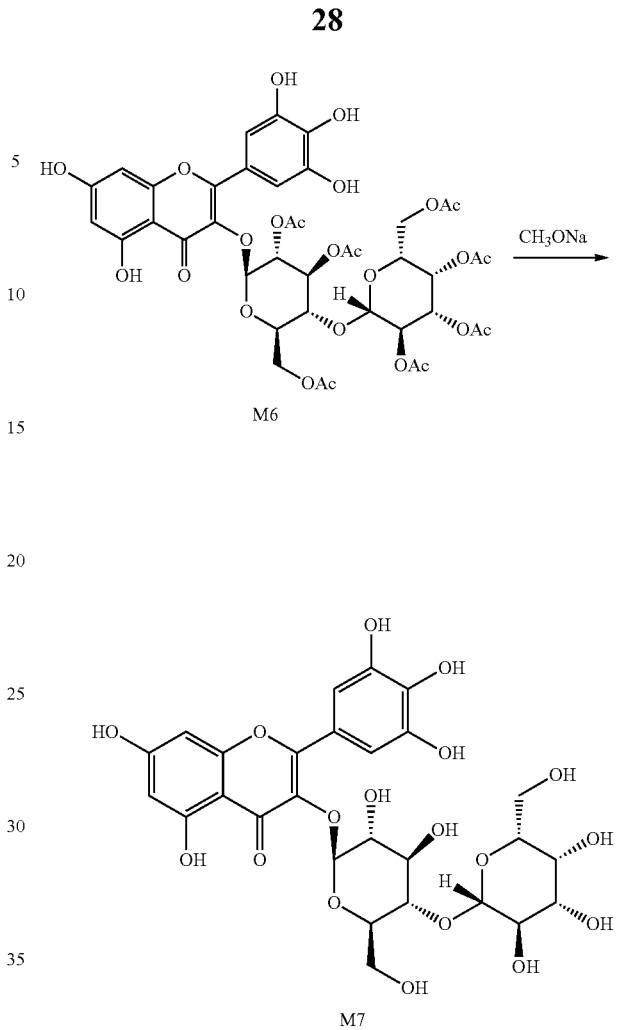

Myricetin derivative. M5 (14.1 g, 10.9 mmol) obtained in Example 3 was added to a 1:1 mixture of methanol/dichloromethane (600 mL), then added with 10% Pd/C (6.4 g) and hydrogenated. The reaction was run at 25° C. for 48 hours. The mixture was filtered and the resulting filtrate was concentrated and evaporated to give 10 g of myricetin derivative M6 as a yellowish solid with 98% yield.

$^1$H NMR (500 MHz, DMSO-$d_6$) δ=12.58 (s, 1H), 10.88 (s, 1H), 9.20 (s, 2H), 8.88 (s, 1H), 7.09 (s, 2H), 6.37 (s, 1H), 6.19 (s, 1H), 5.59 (d, J=7.8 Hz, 1H), 5.23-5.19 (m, 2H), 5.16-5.05 (m, 2H), 4.81 (d, J=9.9 Hz, 1H), 4.74 (d, J=8.0 Hz, 1H), 4.23 (s, 1H), 4.15 (d, J=11.4 Hz, 1H), 4.00 (d, J=6.8 Hz, 2H), 3.93-3.84 (m, 2H), 3.77 (d, J=8.9 Hz, 1H), 2.09 (s, 3H), 2.02-1.96 (m, 9H), 1.94 (s, 3H), 1.88 (s, 3H), 1.85 (s, 3H) ppm. $^{13}$C NMR (125 MHz, DMSO-$d_6$) δ=177.20, 170.37, 170.34, 170.31, 169.95, 169.76, 169.66, 169.45, 164.71, 161.67, 157.60, 156.68, 145.79 (2C), 137.32, 133.21, 119.83, 108.88 (2C), 104.30, 100.29, 99.14, 98.67, 93.91, 76.34, 72.79, 72.30, 72.05, 70.74, 70.02, 69.25, 67.43, 61.78, 61.17, 20.96, 20.91 (2C), 20.80, 20.73 (2C), 20.56 ppm. ESI-MS: (m/z, %)=935 [M−H]$^−$.

Example 5

The synthetic route of myricetin derivative M7 is as follows:

Sodium (0.4 g, 17.1 mmol) was added to anhydrous methanol (60 mL). Upon completion of the reaction, myricetin derivative M6 (4.0 g, 4.3 mmol) was slowly added. The mixture reacted at room temperature for 3 hours, added with ion-exchange resin to adjust the pH to be acidic, stirred for 30 minutes and then filtered. The resulting filtrate was concentrated and evaporated to give 2.3 g of myricetin derivative M7 as a yellowish solid with 85% yield.

$^1$H NMR (500 MHz, DMSO-$d_6$) δ=12.58 (s, 1H), 10.81 (s, 1H), 9.19 (s, 2H), 8.88 (s, 1H), 7.18 (s, 2H), 6.35 (d, J=2.0 Hz, 1H), 6.20 (d, J=2.0 Hz, 1H), 5.52 (d, J=7.5 Hz, 1H), 5.31 (d, J=4 Hz, 1H), 5.10 (d, J=4 Hz, 1H), 4.76-4.74 (m, 2H), 4.65 (t, J=5.5 Hz, 1H), 4.51 (d, J=4.5 Hz, 1H), 4.29 (t, J=5.5 Hz, 1H), 4.22 (d, J=7.5 Hz, 1H), 3.70-3.67 (m, 1H), 3.61 (s, 1H), 3.56-3.50 (m, 2H), 3.49-3.45 (m, 2H), 3.43-3.37 (m, 3H), 3.32-3.26 (m, 3H) ppm. $^{13}$C NMR (125 MHz, DMSO-d6) δ=177.65, 164.55, 161.68, 156.75, 145.83 (2C), 137.11, 133.84, 120.42, 108.92 (2C), 104.39, 104.37, 101.04, 99.08, 93.80, 81.18, 76.02, 75.85, 75.29, 74.07, 73.68, 70.97, 68.63, 61.04, 60.86 (2C) ppm. ESI-MS: (m/z, %)=643 [M+H]$^+$.

Example 6

The synthetic route of myricetin derivative M6' is as follows:

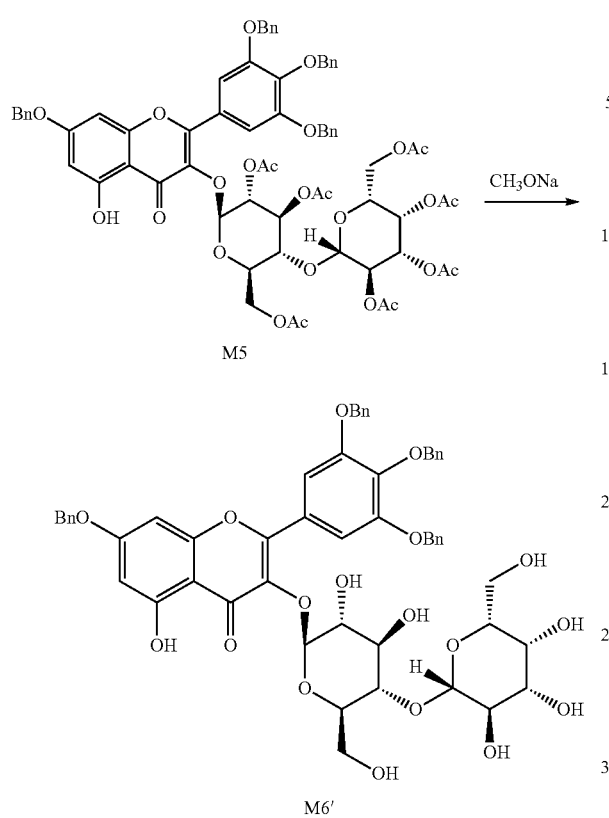

M5

M6'

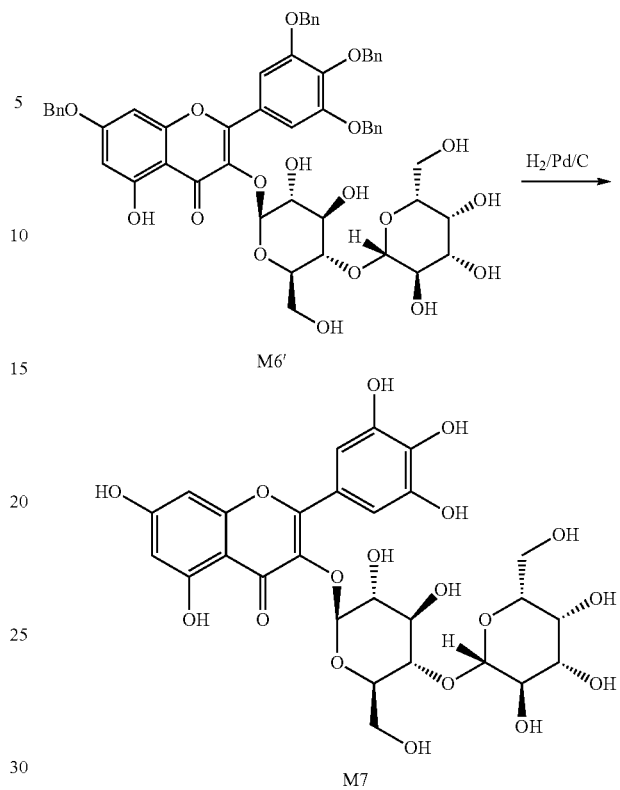

M6'

M7

Myricetin derivative M5 (23 g, 17.73 mmol) was added to anhydrous methanol (230 mL), 5.4 mol/L sodium methoxide in methanol (6.6 mL) was slowly added dropwise at room temperature, followed by continuous stirring for 4 hours. Upon completion of the reaction, tetrahydrofuran (230 mL) was added, followed by addition of cation-exchange resin to adjust the pH to be acidic. The mixture was continuously stirred for 12 hours and filtered to give M6'. The filtrate was directly used for the next step reaction without concentration.

$^1$H NMR (500 MHz, DMSO-$d_6$) δ=12.47 (s, 1H), 7.81-7.17 (m, 22H), 6.84 (s, 1H), 6.52 (s, 1H), 5.68 (d, J=7.6 Hz, 1H), 5.55 (d, J=5.1 Hz, 1H), 5.29-5.22 (m, 4H), 5.17 (t, J=11.9 Hz, 3H), 5.11-5.02 (m, 3H), 4.80-4.72 (m, 2H), 4.65 (t, J=5.0 Hz, 1H), 4.60 (t, J=5.3 Hz, 1H), 4.50 (d, J=4.5 Hz, 1H), 4.11 (d, J=7.5 Hz, 1H), 3.64 (d, J=6.1 Hz, 3H), 3.52 (dd, J=10.5, 5.3 Hz, 1H), 3.50-3.44 (m, 2H), 3.44-3.38 (m, 1H), 3.35 (m, 3H), 3.25 (s, 1H) ppm. $^{13}$C NMR (125 MHz, DMSO-$d_6$) δ=178.06, 164.78, 161.46, 156.75, 156.43, 152.37 (2C), 139.92, 137.89, 137.24 (2C), 136.49, 134.44, 130.10, 129.01 (2C), 128.92 (4C), 128.63 (2C), 128.57 (2C), 128.42 (1C), 128.38 (1C), 128.28 (2C), 128.04 (4C), 125.67, 109.99, 108.89, 105.73, 104.44, 100.91, 99.10, 93.98, 80.66, 75.90, 75.64, 74.97, 74.86 (2C), 74.59, 73.75, 71.01 (2C), 70.97, 70.55, 68.42, 60.58, 59.99 ppm. ESI-MS: (m/z, %)=1001 [M−H]$^−$.

Example 7

The synthetic route of myricetin derivative M7 is as follows:

The filtrate obtained in Example 6 was added with 10% Pd/C (4.6 g) and hydrogenated. The reaction was run at 25° C. for 48 hours. The mixture was filtered and the resulting filtrate was then concentrated and evaporated to give 11 g of M7 as a yellowish solid with overall 97.3% yield of the two steps aforementioned.

$^1$H NMR (500 MHz, DMSO-$d_6$) δ=12.64 (s, 1H), 10.85 (s, 1H), 9.19 (s, 2H), 8.88 (s, 1H), 7.18 (s, 2H), 6.37 (d, J=2.0 Hz, 1H), 6.20 (d, J=2.0 Hz, 1H), 5.51 (d, J=7.5 Hz, 1H), 5.31 (d, J=4 Hz, 1H), 5.10 (d, J=4 Hz, 1H), 4.77-4.75 (m, 2H), 4.65 (t, J=5.5 Hz, 1H), 4.51 (d, J=4.5 Hz, 1H), 4.29 (t, J=5.5 Hz, 1H), 4.20 (d, J=7.5 Hz, 1H), 3.70-3.67 (m, 1H), 3.61 (s, 1H), 3.56-3.50 (m, 2H), 3.49-3.45 (m, 2H), 3.43-3.38 (m, 3H), 3.32-3.26 (m, 3H) ppm. $^{13}$C NMR (125 MHz, DMSO-d6) δ=177.75, 164.55, 161.68, 156.71, 145.83 (2C), 137.11, 133.83, 120.42, 108.92 (2C), 104.39, 104.35, 101.04, 99.08, 93.81, 81.18, 76.00, 75.85, 75.29, 74.06, 73.68, 70.97, 68.61, 61.04, 60.85 (2C) ppm. ESI-MS: (m/z, %)=643 [M+H]$^+$.

Example 8

Determination of the therapeutic effects of myricetin derivative M5, M6 and M7 on dextran sulfate sodium (DSS)-induced chronic colitis in mice
Experimental Materials and Methods
1, Experimental Materials:
1. Compounds tested and control drugs: myricetin derivative M5, M6 and M7, positive control drug-sulfasalazine (SASP, from Sigma); control drug-myricetin;
Experimental animals: C57BL/6 mice, 20 to 22 g, both male and female, SPF grade provided by Charles River Laboratories, Beijing.
Experimental site: Animal Experimental Platform Laboratory of Capital Medical University; mice were fed with standard animal feed.

2. DSS-induced chronic colitis model in mice: 36 C57BL/6 mice were randomly divided into six groups, with six mice in each group. DSS (0.5 g) was weighed and dissolved in 50 ml of purified water, for 6 mice to drink in one day. The DSS water was made freshly and was provided at fixed time on a daily basis for 7 days successively, which was then replaced by freshly-made purified drinking water for the next successive 14 days. The same procedure was repeated successively for 3 times. Each group of mice was given the same treatment for the preparation of chronic colitis model.
3. Drug preparation method:
3.1 Solvent control group: 0.5 mL of DMSO was added to 10 mL of 0.5% CMC-Na.
3.2 Myricetin derivative M5 and M6 tested: 100 mg of M5 and M6 each was weighed and dissolved in 0.5 ml of DMSO, and diluted to 10 mL with 0.5% CMC-Na.
3.3 Myricetin derivative M7 tested: 100 mg of M7 was weighed and dissolved in 10 mL of 5% sodium bicarbonate injection.
3.4 Myricetin control: 100 mg of myricetin was weighed and dissolved in 10 mL of 0.5% CMC-Na.
3.5 Sulfasalazine (SASP): 100 mg of SASP was weighed and dissolved in 10 mL of saline.
4. Administration method: the body weight of mice was weighed daily, and drugs were administered 0.01 ml/g (100 mg/kg) consecutively for 18 days.
5. Animal observation and treatment method: body weight, diet, diarrhea (or bloody stools) etc. were observed daily. At the end of the experiment, mice were sacrificed for dissection. The colon and small intestine were dissected out for visual observation and pathological analysis. Pathological examination methods and evaluation criteria: the colons of each group were fixed with 10% formalin followed by routine paraffin embedding, sectioning and HE staining. The degree of colonic inflammation in each group was evaluated under microscope. According to the degree of inflammatory cell infiltration in colonic lamina propria, the following grading criteria were established: level 0, no obvious inflammatory cell infiltration; +(level 1), slight inflammatory cell infiltration; ++(level 2), moderate inflammatory cell infiltration; +++(level 3), severe inflammatory cell infiltration and may be accompanied by necrosis or loss of mucosal cells.

The experimental results are as follows:
1. The symptoms of DSS-induced chronic colitis in mice: all groups of mice (100%) showed diarrhea, decreased diet, loss of body weight and declined fur gloss, indicating successful setting-up of chronic colitis model in mice.
2. The general symptoms of mice in each group: mice in M7 group showed a significant reduction in diarrhea since the 5$^{th}$ day of drug administration onwards, among which 4 mice had no obvious diarrhea and showed increased fur gloss; mice in M6 group showed slight reduction in diarrhea, among which 1-2 mice had no obvious diarrhea; mice in M5 group showed no significant reduction in diarrhea; mice in myricetin control group and SASP group showed slight reduction in diarrhea.

Figure 2:
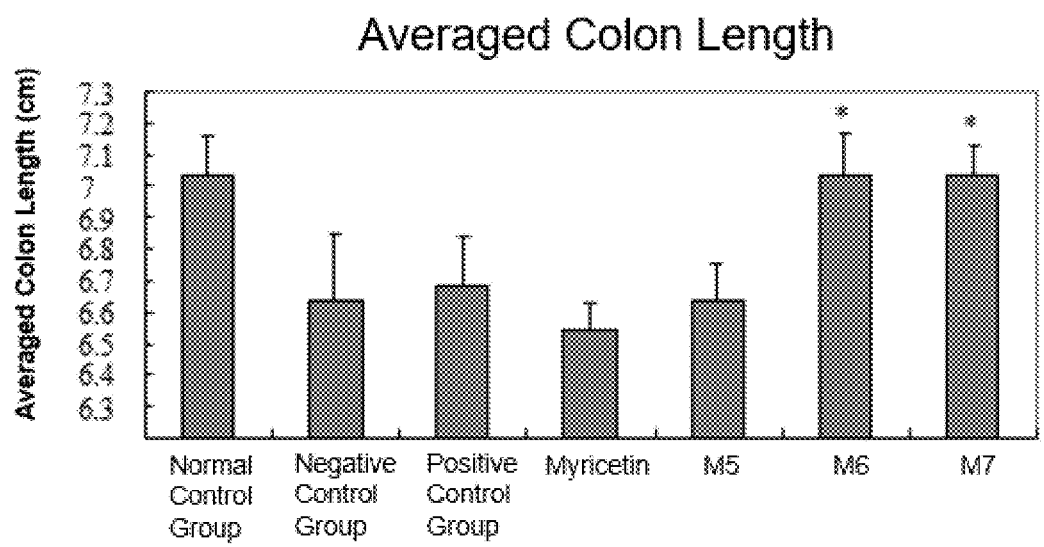
FIG. 2 illustrates the results of colon length (cm) of each group of mice at the end of drug administration in Example 8, * P<0.05 comparing to model group.

The changes in body weight of mice in each group during drug administration were shown in FIG. 1. Statistical analysis showed that there was no significant difference in the averaged body weight between the groups or the observation time points, indicating oral administration of the compounds had no obvious toxic effect.
3. Colon length of mice in each group: The colon (from the ileocecal end to the anal end) was dissected at the end of the experiment and the colon length of each group was measured. The results were shown in FIG. 2. Comparing to the normal control group, the colon length of mice in the model group was significantly shortened (P<0.05). The averaged colon lengths of mice in M7 and M6 groups were similar to that of normal control group, and was significantly longer than that of the model group (P<0.05), indicating the compounds had excellent inhibitory activity against chronic colonic inflammation. Mice in other groups showed no significant difference in colon length from the model group.

Figure 3:
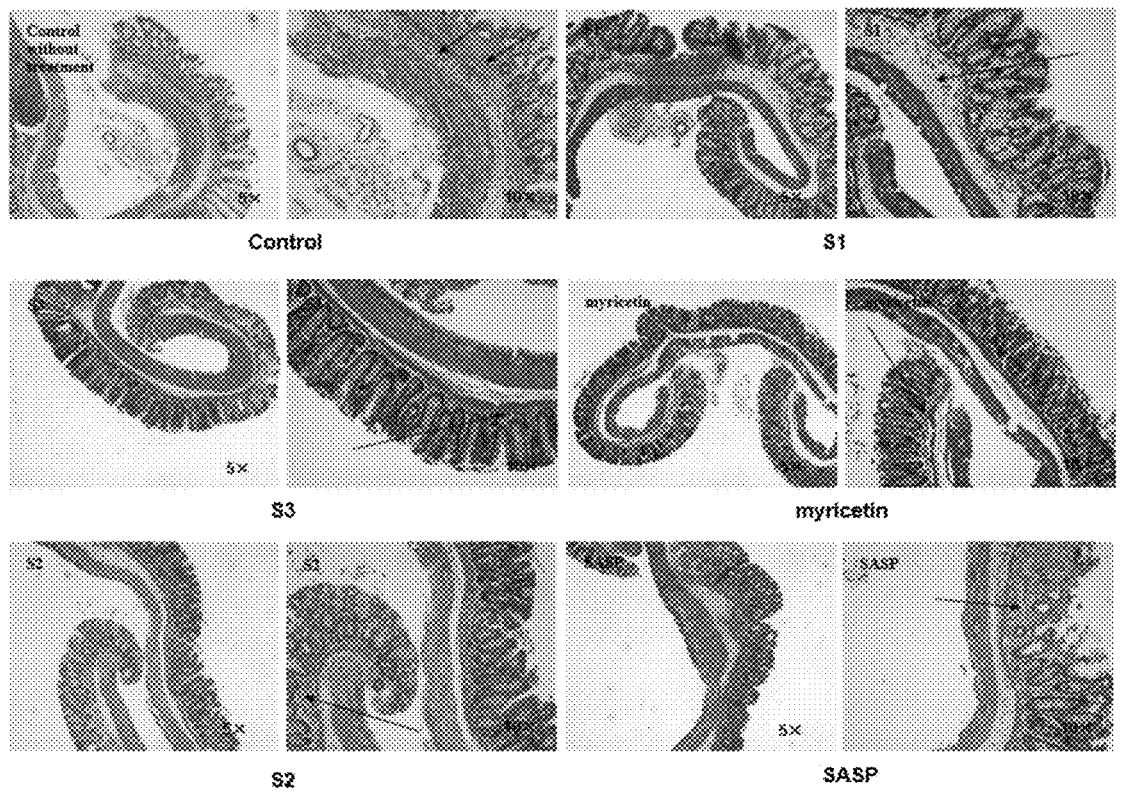
FIG. 3 illustrates the therapeutic effect of myricetin derivative M5, M6 and M7, myricetin and sulfasalazine (SASP) on DSS-induced chronic colitis in mice in Example 8 (pathological examination results: arrows indicate local colonic tissue with significant inflammation as indicated by infiltration of inflammatory cells such as lymphocytes).

The results indicated that comparing to myricetin and its derivative M5, M6 and M7 have significant pharmacological activities of inhibiting chronic colitis.
4. Pathological examination of mice colon in each group: In the model group, the infiltration of a large number of lymphocytes was shown in the lamina propria of colonic mucosa and submucosa. The intestinal tissues of each layer were loose. The muscular layer also contained infiltrating lymphocytes. Cell shedding in the epithelial lining was also seen. The degree of chronic colonic inflammation was significantly alleviated in the M7-treated group. According to the four-level evaluation criteria for chronic colonic inflammation, myricetin derivative M7 displayed a significant inhibitory activity against chronic colonic inflammation in mice, as shown in FIG. 3 and Table 1. The myricetin control group also had some pharmacological effect, and the degree of inflammation was + based on the above-mentioned grading criteria. Other treatment groups showed no significant improvement on colonic inflammation, as shown in Table 1.

TABLE 1

Pathological grading scores for chronic inflammation of colon in each group of mice (n = 3)

| | Grading scores for chronic inflammation of colon | | | |
|---|---|---|---|---|
| Groups | 0 | + | ++ | +++ |
| Model Group | | | | 3 |
| M7 Group | 3 | | | |
| M6 Group | 1 | 2 | | |
| M5 Group | | | 1 | 2 |
| Myricetin Group | 1 | 1 | 1 | |
| SASP Group | | | 1 | 2 |

Note:
3 mice were examined in each group, and the numbers in the table were mice colons actually observed in each group.

DSS-induced chronic colitis in mice is a classic method and a basic animal model for studying and evaluating the activity of compounds against chronic colitis and drug screening, wherein colon pathological analysis is the basic standard for determining the effectiveness of drugs. In the present experiments, myricetin derivative M7 significantly reduced the degree of colon inflammation and significantly alleviated general clinical symptoms of chronic colitis in mice, while the pharmacological activity of the rest compounds and control drug-SASP was weaker than that of myricetin derivative M7.

In vitro experiments also indicated that there was no obvious cytotoxic effect of myricetin and its derivative (where mouse peritoneal macrophage RAW264.7 was incubated with myricetin and myricetin derivative such as M5, M6 and M7, respectively for 24 hours, no significant inhibitory effect was observed on cell proliferation, even when the dose was increased to 20 μM). Therefore, this series of compounds may be considered suitable for drug development for treating chronic colitis and inflammatory bowel disease.

Example 9

The synthetic route of myricetin derivative M8 is as follows:

M7 (0.64 g, 1 mmol) was added to 0.1N potassium hydroxide solution (10 mL, 1 mmol), and the reaction mixture was stirred at room temperature for 3 hours, concentrated and evaporated to give 0.66 g of M8 as a yellowish solid with 99% yield.

$^1$H NMR (500 MHz, DMSO-$d_6$) δ=12.49 (s, 1H), 7.17 (s, 2H), 5.89 (s, 1H), 5.72 (s, 1H), 5.32 (d, J=6.0 Hz, 1H), 4.22 (d, J=6.6 Hz, 1H), 3.67-3.60 (m, 2H), 3.49 (m, 4H), 3.38 (m, 3H), 3.32-3.29 (m, 3H) ppm.

Example 10

The synthetic route of myricetin derivative M9 is as follows:

M7 (0.64 g, 1 mmol) was added to 0.1 N calcium hydroxide solution (10 mL, 1 mmol). The reaction mixture was stirred at room temperature for 1 hour, then heated to 75° C. for 1 hour, concentrated and evaporated to give 0.66 g of M9 as a blackish solid with 99% yield.

$^1$H NMR (500 MHz, DMSO-$d_6$) δ=7.15 (s, 2H), 6.34 (s, 1H), 6.21 (s, 1H), 5.51 (d, J=6.4 Hz, 1H), 4.22 (d, J=6.8 Hz, 2H), 3.67 (d, J=11.5 Hz, 4H), 3.61 (s, 3H), 3.54 (d, J=6.5 Hz, 4H), 3.50-3.44 (m, 6H), 3.44-3.36 (m, 5H), 3.35 (t, J=9.2 Hz, 9H) ppm.

Example 11

The synthetic route of myricetin derivative M10 is as follows:

M7 (0.64 g, 1 mmol) was added to 0.1N sodium hydroxide solution (10 mL, 1 mmol), and the reaction mixture was stirred at room temperature for 3 hours, concentrated and evaporated to give 0.66 g of M10 as a yellowish solid with 99% yield.

$^1$H NMR (500 MHz, DMSO-$d_6$) δ=12.47 (s, 1H), 7.17 (s, 2H), 5.92 (s, 1H), 5.75 (s, 1H), 5.32 (d, J=6.5 Hz, 1H), 4.22 (d, J=6.8 Hz, 1H), 3.71-3.58 (m, 2H), 3.58-3.43 (m, 4H), 3.38 (m, 3H), 3.34-3.22 (m, 3H) ppm.

Example 12

Water solubility test for myricetin derivative M5, M6 and M10

Instrument: Waters Alliance e2695 LC/MS; chromatographic column: Waters×Bridge C18 4.6×150 mm.

Testing Steps:

1. Preparation of the standard curve:

Appropriate amount of said myricetin derivative was weighed and dissolved in methanol to prepare a solution of 1 mg/ml respectively, which was diluted with methanol to different concentrations of working solution as standard samples for testing.

Wherein the different concentrations of working solutions were obtained through sequential dilution: 100,000, 10,000, 5,000, 2,500, 500, 250, 100, 50, 20, 10 ng/mL.

2. 1 mL of ultrapure water was added into a 1.5 ml transparent EP tube. Appropriate amount of said myricetin derivative was each added into a transparent EP tube, followed by vortex mixation and ultrasonication till the drug was no longer dissolved (the solution appeared cloudy or had suspended particles). The mixture was then placed in an incubating oscillator for shaking at the temperature of (37±1) ° C., 100 r/min, for 24 hours, to achieve a sufficient solubility balance. 24 hours later, the saturated solution was taken out for centrifugation at 3000 r/min for 15 min. The supernatant was immediately filtered through a 0.45 μm microporous membrane, and the initial part of the filtrate was discarded. Samples were added for chromatography. The peak area was measured and the equilibrium solubility of each compound in pure water was calculated using a standard curve. The experimental results were shown in Table 2.

TABLE 2

Solubility test results of myricetin derivative M5, M6 and M10

| Samples | Incubation temperature | Incubation time | Solubility |
|---|---|---|---|
| M5 | 37° C. | 24 h | <100 ng/mL |
| M6 | 37° C. | 24 h | 1395.51 ng/mL |
| M10 | 37° C. | 24 h | >0.1 g/mL |

According to the experimental results in Table 2, the solubility of myricetin derivative M5 was very low, but myricetin derivative M10 had excellent solubility.

Example 13

Determination of therapeutic effect of myricetin derivative M10 on azomethane (AOM)/dextran sulfate sodium (DSS)-induced chronic ulcerative colitis and inflammation-associated tumorigenesis.

Experimental Materials and Methods

1. Experimental Materials:

Compound tested and control drugs: myricetin derivative M10, control compound myricetin, aspirin (Sigma).

Experimental animals: C57BL/6 mice, 20 to 22 g, both male and female, SPF grade provided by Beijing Vital Lihua Experimental Animal Company, and mice were fed with standard animal feed.

Test site: Animal laboratory of the Basic Research building of Capital Medical University.

2. Animal model for chronic colitis and inflammation-associated tumorigenesis, and grouping method:

Animal models of AOM/DSS-induced chronic colitis and inflammation-associated tumorigenesis: 48 C57BL/6 mice were randomly divided into six groups with eight mice in each group, including model group, for which 0.5% CMC-Na was administered intragastrically every day; aspirin group, for which 100 mg/kg of aspirin (dissolved in 0.5% CMC-Na) was administered intragastrically; myricetin control group, for which 100 mg/kg of myricetin (dissolved in 0.5% CMCNa) was administered intragastrically; M10 high dose group, for which 100 mg/kg of M10 (dissolved in pure water) was administered intragastrically; M10 medium dose group, for which 50 mg/kg of M10 (dissolved in pure water) was administered intragastrically; M10 low dose group, for which 25 mg/kg of M10 (dissolved in pure water) was administered intragastrically.

Preparation of chronic ulcerative colitis mice model: said groups of mice were intraperitoneally injected with 10 mg/kg of azoxymethane (AOM) on day one. Purified drinking water containing 2% dextran sulfate sodium (DSS) was freshly made and provided on day one and on the next six consecutive days, the replaced by purified drinking water for the next seven consecutive days. The above procedure was then repeated for 3 more times.

3. Administration method:

Solvent control group: 0.5% CMC-Na solution was made.

M10-treated group: 200 mg of M10 was weighed and dissolved in 10 mL of 0.5% CMC-Na solution (20 mg/mL), and consecutively diluted 2 times and 5 times for future use. 0.2 mL of each prepared solutions was given intragastrically to mice (the body weight was assumed as 20 g per mouse), namely divided into high, medium or small dose groups.

Myricetin control group: 200 mg of myricetin was weighed and dissolved in 10 mL of 0.5% CMC-Na.

Aspirin-treated group: 200 mg of aspirin was weighed and dissolved in 10 mL of 0.5% CMC-Na.

Administration method: The body weight of mice was measured daily, and drugs were administered at 0.01 mL/g (100 mg/kg) per day for 12 consecutive weeks.

4. Animal observation and treatment methods: weight, diet, diarrhea (or bloody stools) etc. were observed daily.

At the end of the experiment, mice were sacrificed. The colon and small intestine were dissected out for visual observation and pathological analysis. Pathological examination methods and evaluation criteria: the mice colons of each group were fixed with 10% formalin, followed by routine paraffin embedding, sectioning and HE staining. The developmental degree of colonic inflammation and colon cancer in each group of mice was evaluated under microscopic observation.

The experiment results are as follows:

(1) M10 significantly alleviated the symptoms of AOM/DSS-induced chronic colitis in mice: all groups of mice (100%) showed diarrhea, decreased diet, loss of body weight and declined fur gloss after model preparation. On the fourth day after the start of each cycle of DSS administration, symptoms like loss of body weight, declined fur gloss, loose stools, occult blood, blood in the stool, etc. started to appear, which was not alleviated until the $10^{th}$ day of normal drinking water administration. Moreover, on the $3^{rd}$ day after the start of the $4^{th}$ round of DSS administration, severe loss of body weight and blood in the stool, etc. were observed, which was not alleviated until the $3^{rd}$ day of normal drinking water administration. The symptoms gradually worsened after each round of DSS administration. The above-mentioned symptoms in all three dose groups of M10 were significantly alleviated than the aforementioned groups. At the end of the $4^{th}$ round, the mice in each dose group of M10 gained back their normal body weights faster than the aforementioned groups, and the condition of M10-treated mice were stable during the time when normal drinking water was administered.

Figure 4:
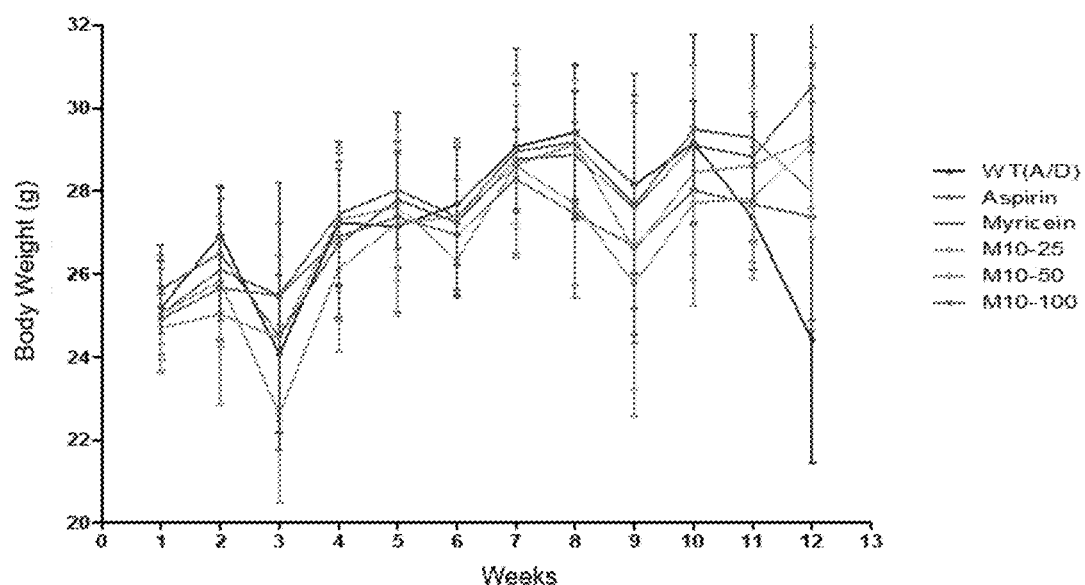
FIG. 4 illustrates the changes in body weight of each group of mice during drug administration in Example 13.

(2) M10 treatment significantly prevented the loss of body weight induced by AOM/DSS: Statistical analysis showed that there was no significant difference in the averaged body weight between groups or observation time points, indicating oral administration of said compounds had no obvious toxic effect. The body weight of mice in model group decreased significantly between week 10 and 12, while the body weight of mice in other treatment groups did not decrease, as shown in FIG. 4.

Figure 5:
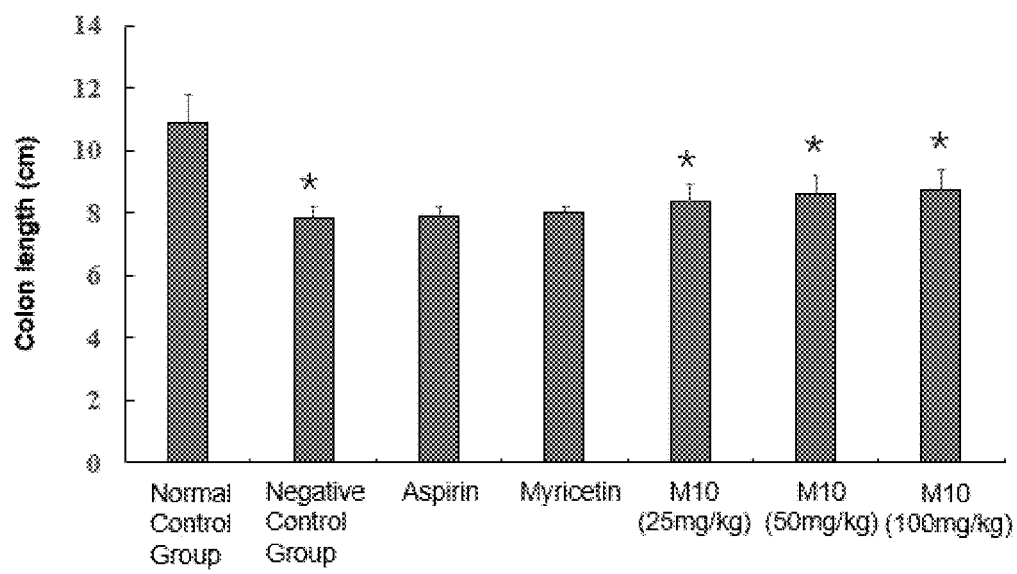
FIG. 5 illustrates the colon length of each group of mice at the end of drug administration in Example 13.

(3) M10 treatment prevented the shortening of colon length in AOM/DSS-induced colitis: FIG. 5 showed the colon length of each group of mice. At the end of the experiment colons were dissected out from each group of mice for measurement of the length. Comparing to the colon length in normal control group, the colon length in model group was significantly shortened (P<0.05), while the averaged colon length of M10-treated mice in all dose groups was similar to that of mice in normal control group, and significantly longer than that of mice in aspirin-treated group and myricetin control group, indicating the inhibitory effect of M10 on chronic colitis, no significant difference between other groups and the model group was found.

(4) M10 treatment significantly inhibited AOM/DSS-induced colon cancer: the results of the following two experiments indicated that M10 had a relatively strong therapeutic effect on colon cancer.

Figure 6:
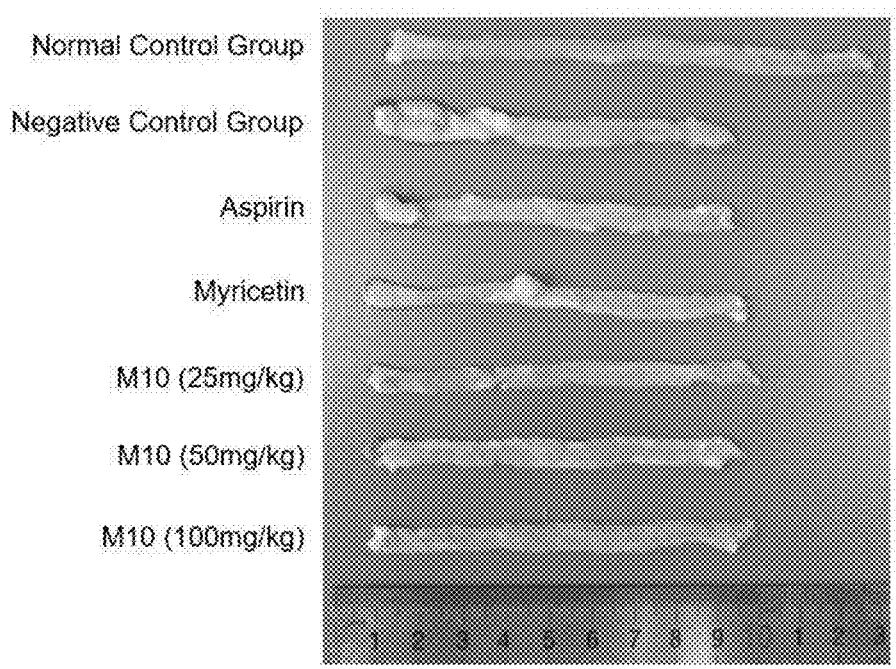
FIG. 6 illustrates the amounts of colon cancer nodules of each group of mice at the end of drug administration in Example 13.
Figure 7:
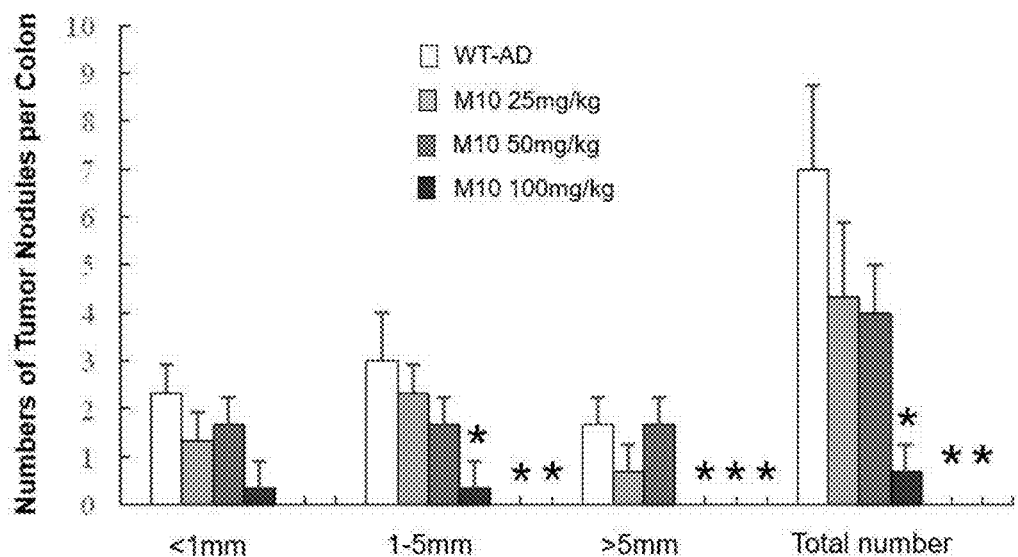
FIG. 7 illustrates the diameters of colon cancer nodules of each group of mice at the end of drug administration in Example 13.

① M10 treatment significantly inhibited the number of colon cancer nodules induced by AOM/DSS: mice colon was dissected after 12 weeks of drug administration. The colon was washed with saline and the length of colon was measured. The number of tumor nodules in the whole length of colon was counted and categorized into three groups, namely <1 mm, 1-5 mm and >5 mm, based on diameters of the nodules. The results showed that M10 at all doses significantly reduced the number of tumor nodules, as shown in FIG. 6 and FIG. 7.

Figure 8:
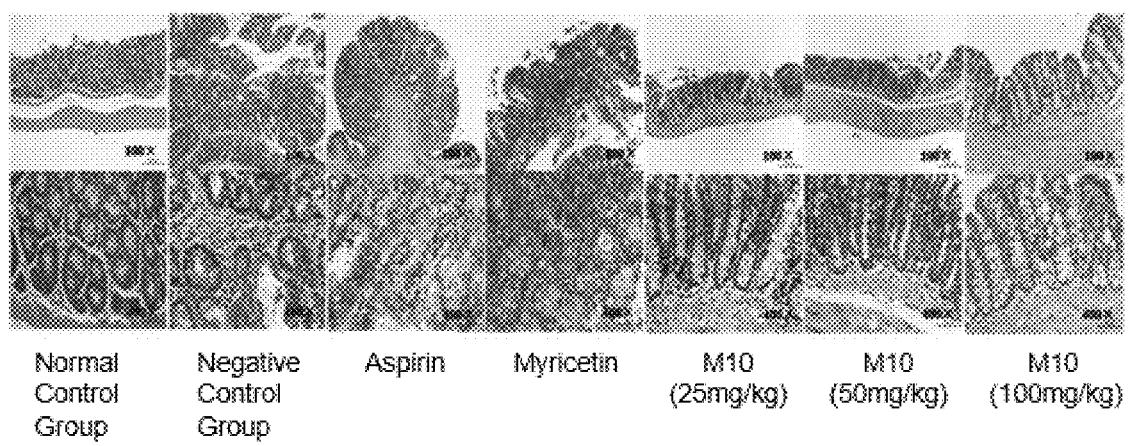
FIG. 8 illustrates the histopathological analyses of colon tissue of each group of mice at the end of drug administration in Example 13.

② Pathological analysis on mice colon tissue: in normal control group, the layers of colon tissue such as mucosa, submucosa and muscle layers were intact and there was no obvious inflammatory cell infiltration. In model group, infiltration of a large number of cancer cells in the colon tissue was observed accompanied by the existence of colon cancer nodules, basic structures of all the colonic tissue layers were damaged, the infiltrating cancer cells were irregularly arranged, the nucleus/cytoplasm ratio was significantly increased, infiltration of inflammatory cells and ulceration were obvious. In aspirin-treated mice, the above-mentioned pathological changes in the colon tissues were alleviated to some extent with noticeable cancer nodules and increased nucleus/cytoplasm ratio in the epithelial cells. In myricetin-treated mice, an inhibitory activity against colon cancer was also observed, indicating a similar therapeutic effect as aspirin. M10 shows significant activity of preventing and treating colon cancer with a certain degree of dose-effect correlation, as indicated by improvement seen in tissue morphology, for example, the epithelial cells in colonic mucosa showed nearly normal structure with only a minor degree of irregular cell arrangement, and the nucleus/cytoplasm ratio was significantly reduced comparing to that of model group, as shown in FIG. 8.

Figure 9:
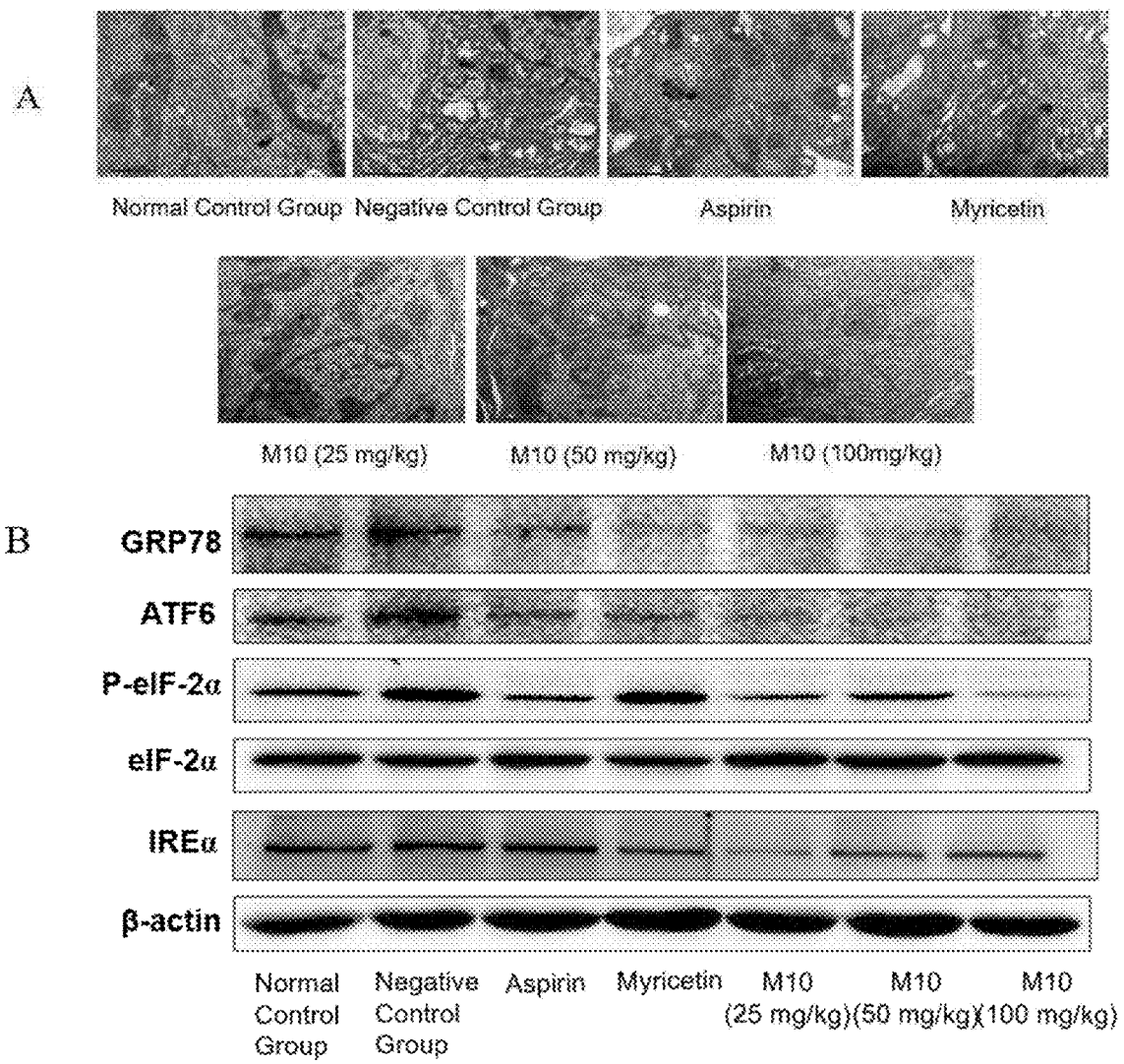
FIG. 9 illustrates the mechanism of M10 in inhibiting endoplasmic reticulum stress induced by AOM/DSS in Example 13.

FIG. 9A showed swollen endoplasmic reticulum membrane, irregular fracture arrangement etc, which were significantly alleviated by M10 treatment. FIG. 9B showed an upregulation of AOM/DSS-induced endoplasmic reticulum stress signaling molecules GRP78, ATF6, PelF-2a and IREa, which may further trigger inflammation, while the above-mentioned activation of stress signaling molecules was significantly inhibited by M10 treatment. In summary, M10 significantly inhibited AOM/DSS-induced endoplasmic reticulum stress response.

Figure 10:
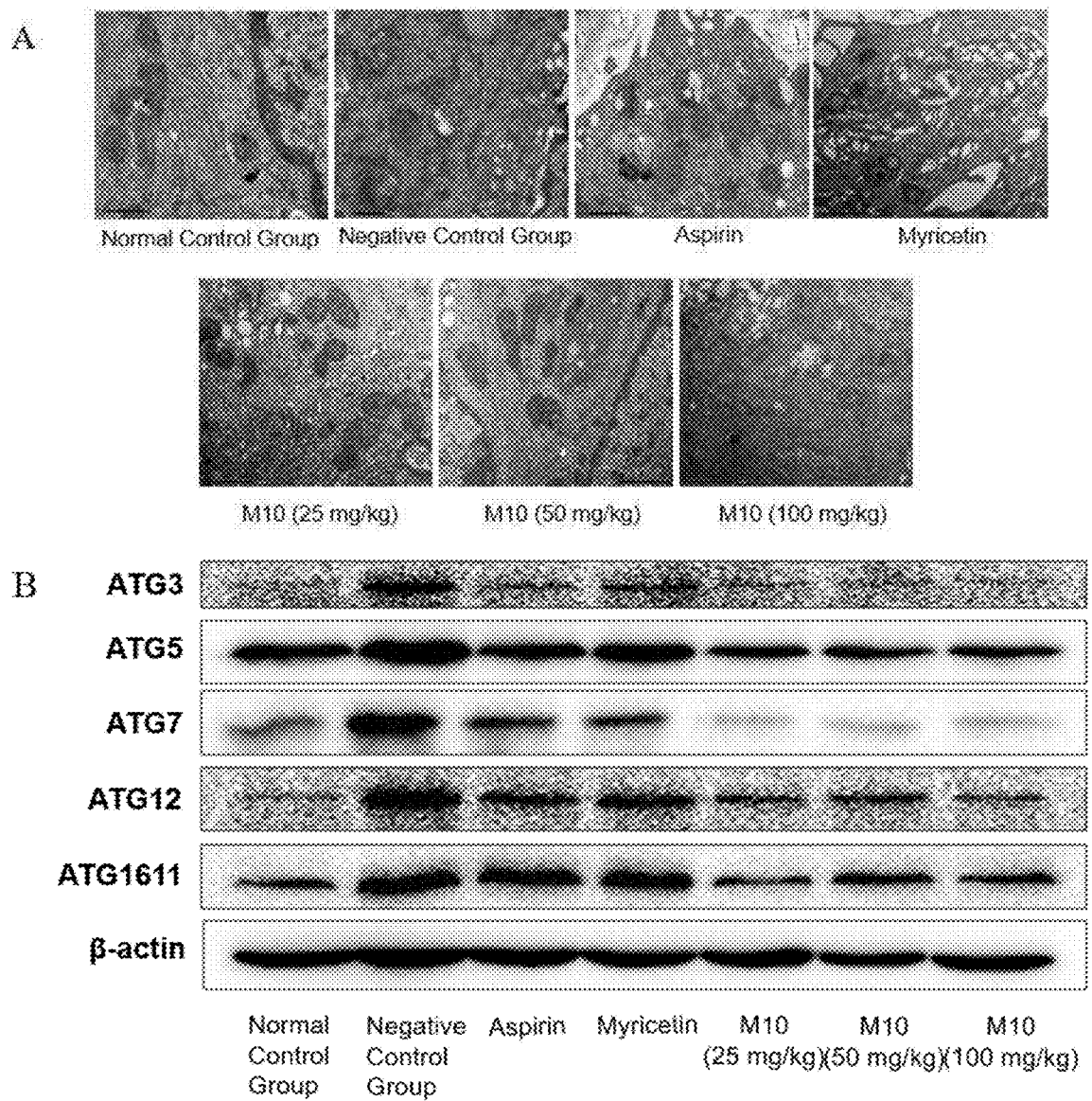
FIG. 10 illustrates the mechanism of M10 in inhibiting cellular autophagy and colonic epithelial cell proliferation and carcinogenesis caused by AOM/DSS-induced endoplasmic reticulum stress in Example 13.

FIG. 10A showed autophagic vacuoles formed by colonic epithelial cells in response to endoplasmic reticulum stress accompanied by mitochondrial swelling etc, which was significantly alleviated after M10 treatment. FIG. 10B showed significant upregulation of signaling molecules ATG3, ATG5, ATG7, ATG12, and ATG1611 resulting from AOM/DSS-induced endoplasmic reticulum stress, indicating an upregulation of autophagosomes; whereas M10 significantly inhibited the activation of the above-mentioned signaling molecules and thereby was able to inhibit the autophagy process. In summary, M10 significantly inhibited cellular autophagy induced by AOM/DSS-induced endoplasmic reticulum stress response and thereby inhibited the proliferation and carcinogenesis of colonic epithelial cells.

Example 14

Acute Toxicity Experiment on Myricetin Derivative M10, Testing Maximum Tolerated Dose in Mice.
Experimental Animals:
Animal germ line: KM mice
Animal grade: SPF grade
Gender and number: 10 females; 10 males;
Animal's age at the start of the experiment: 5 to 6 weeks old
Animal's body weight at the start of the experiment: 18 to 22 g
Animal Source: Jinan Pengyue Experimental Animal Breeding Co., Ltd.
Laboratory Animal Production License: SCXK (Lu) 20140007
Quarantine:
The experimental animals were examined and quarantined according to corresponding requirements, followed by three days of adaptive observation, monitoring the condition of eyes, ears, nose, mouth, fur, abdomen, vulva, perianal, limbs, claws, toes, gait, behavior, excretion, food intake and water drinking. Mice with quarantine conformity were recruited for experiments.
Grouping:
The KM mice with quarantine conformity were selected for the experiment. 10 mice weighing 18 g-22 g each after fasting were randomly selected, labeled and housed in separate cages.
Feeding Conditions:
Temperature in the laboratory was 20° C.-25° C., humidity was 40%-70%, ventilation frequency was 10-20 times/hour, with light/dark circle 12 hours, and stocking density <5 mice per cage. The breeding environment was strictly in accordance with Nation Standard of the People's Republic of China—Requirement of Environment and Housing Facilities for Laboratory Animals.
Experiment Method:
In accordance with the acute toxicity testing method in Healthy Food Inspection and Evaluation Technical Specifications (2003 edition), sample solutions were prepared and administered twice intragastrically within 24 hours with the maximum dose of 20 mL/kg. Mice were monitored 1, 4, 8, 24, 48, 72, 96, 120, 144, 168 and 336 hours respectively after drug administration, and the maximum tolerable dose in mice was calculated if no mouse died.
The Monitor Record for Maximum Tolerated Dose:
One hour after the end of two intragastric administrations, no abnormalities were found in behavior, reaction ability, fur color, skin, body temperature, the rate, depth or pattern of respiration, secreta from mouth, eyes or nose in mice, indicating the absence of neurotoxic or any other acute toxicity reactions.
Normal food and drinking water were provided 24 hours after drug administration.
No mice died during the fourteen days of observation period after drug administration, and no significant increase in body weight was observed two days after drug administration. According the monitor record during the whole observation period, no obvious toxicity in the samples tested was found.
Results:
According the testing results, the maximum concentration of the samples tested was 250 mg/mL. No death was observed after mice were administered twice intragastrically within 24 hours with the tolerable dose of 0.02 mL/g. The maximum tolerable dose of the sample tested in mice was more than 5 g/kg.

Example 15

The synthetic route of myricetin derivative M13 is as follows:

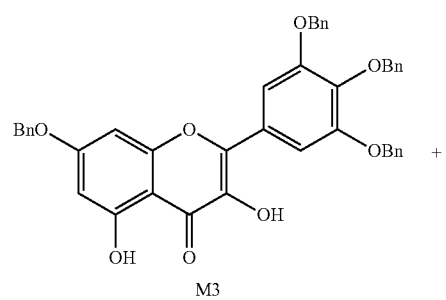

M3

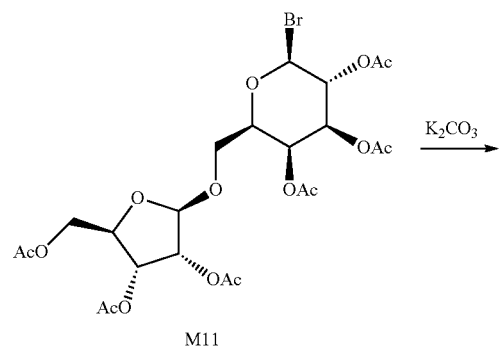

M11

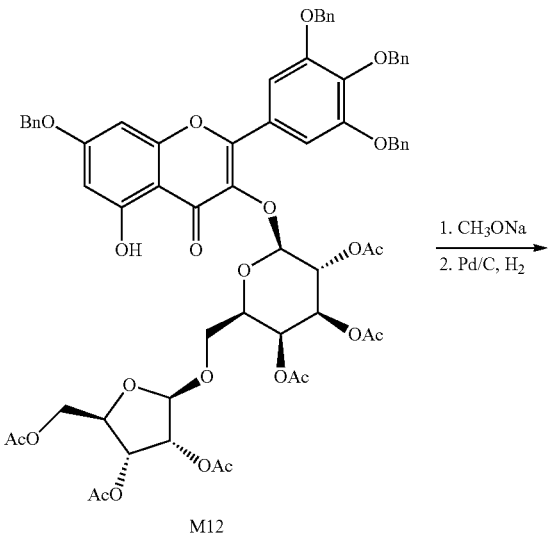

M12

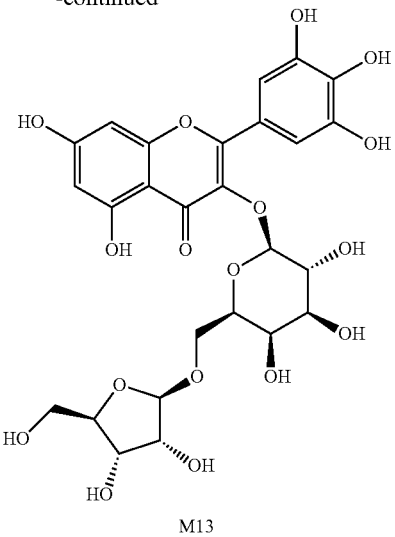

M13

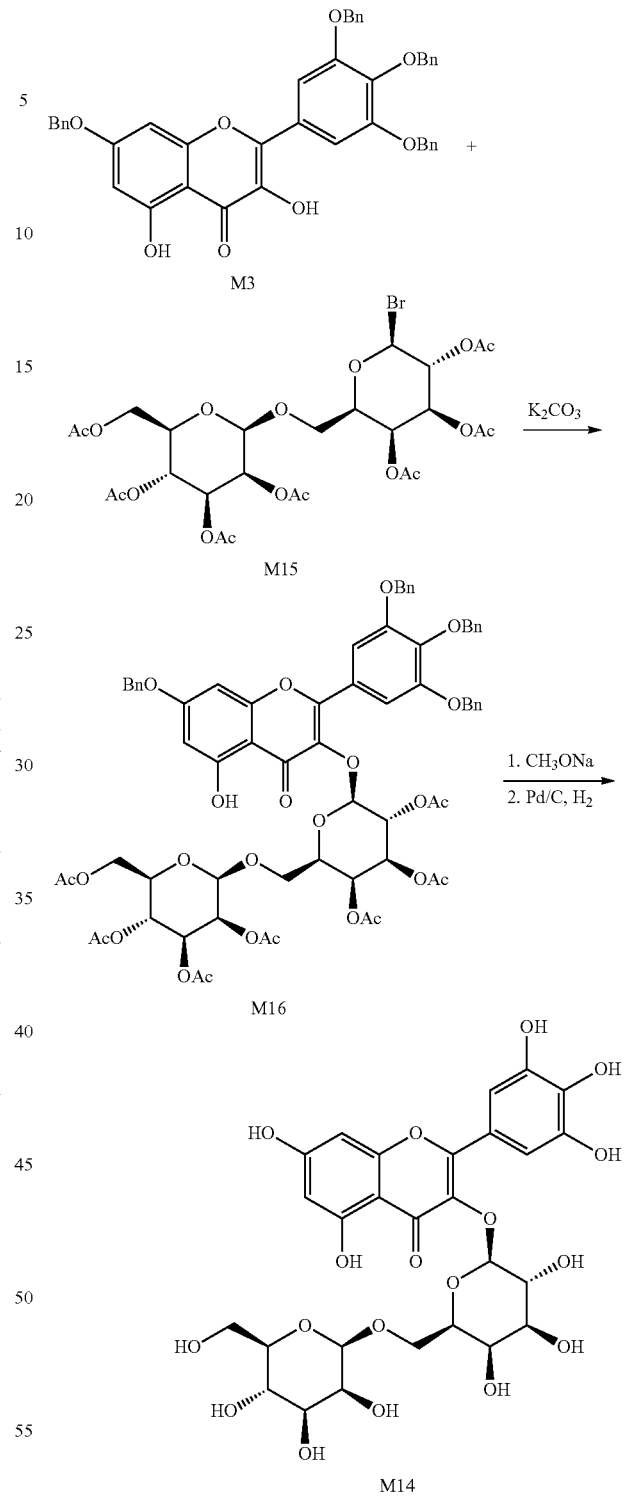

The benzyl-protected myricetin derivative M3 (1 g, 1.48 mmol) was added to dichloromethane (20 mL), followed by consecutive addition of M11 (1.14 g, 1.77 mmol), tetrabutylammonium bromide (0.57 g, 53 mmol) and a 7 mL solution of potassium carbonate (0.76 g, 5.53 mmol). The reaction mixture was heated to 40° C. and stirred for 2 hours. Water was then added for phase separation. The organic phase was washed consecutively with water and brine, then dried. 0.88 g of M12 as a yellowish solid was obtained via column chromatography with 49% yield. M12 (0.88 g, 0.72 mmol) was added to anhydrous methanol (20 mL), and 5.4 mol/L sodium methoxide in methanol (0.5 mL) was slowly added dropwise at room temperature. The reaction mixture was stirred continuously for 4 hours. Upon completion of the reaction, tetrahydrofuran (20 mL) was added, followed by addition of cation-exchange resin to adjust the pH to be acidic. The mixture was stirred for another 2 hours and filtered. The resulting filtrate was directly added with 10% Pd/C (0.2 g) without concentration and hydrogenated. The reaction was run at 25° C. for 24 hours, followed by filtration. The resulting filtrate was concentrated and evaporated to give 0.45 g of M13 as a yellowish solid with overall 97.5% yield of the two steps aforementioned.

$^1$H NMR (500 MHz, DMSO-$d_6$) δ=12.63 (s, 1H), 10.85 (s, 1H), 9.09 (s, 2H), 8.90 (s, 1H), 7.19 (s, 2H), 6.37 (d, J=1.9 Hz, 1H), 6.19 (d, J=1.9 Hz, 1H), 5.32 (d, J=7.6 Hz, 1H), 5.05 (d, J=4.5 Hz, 1H), 4.90 (d, J=5.2 Hz, 1H), 4.86 (d, J=5.5 Hz, 1H), 4.72 (d, J=7.4 Hz, 1H), 4.60 (d, J=5.3 Hz, 1H), 4.52 (d, J=3.4 Hz, 1H), 4.40 (d, J=5.0 Hz, 1H), 3.84-3.70 (m, 2H), 3.57 (d, J=7.7 Hz, 3H), 3.46 (s, 3H), 3.41 (d, J=4.2 Hz, 1H), 3.40-3.37 (m, 2H). $^{13}$C NMR (125 MHz, DMSO-$d_6$) δ=177.33, 164.11, 161.22, 156.31, 156.22, 145.39 (2C), 136.71, 133.64, 124.92, 119.96, 108.54 (2C), 103.85, 101.85, 101.03, 98.67, 93.36, 73.60, 73.12, 71.06, 70.77, 68.89, 68.10, 66.35, 63.59.

Example 16

The synthetic route of myricetin derivative M14 is as follows:

The benzyl-protected myricetin derivative M3 (1 g, 1.48 mmol) was added to dichloromethane (20 mL), followed by consecutive addition of M15 (1.24 g, 1.77 mmol), tetrabutylammonium bromide (0.57 g, 53 mmol) and a 7 mL solution of potassium carbonate (0.76 g, 5.53 mmol). The reaction mixture was heated to 40° C. and stirred for 2 hours. Water was added for phase separation. The organic phase was washed consecutively with water and brine, and dried. 0.95 g of M16 as a yellowish solid was obtained via column chromatography with 50% yield.

Myricetin derivative M16 (0.95 g, 0.73 mmol) was added to anhydrous methanol (20 mL), and 5.4 mol/L sodium methoxide in methanol (0.5 mL) was slowly added dropwise at room temperature. The reaction mixture was stirred continuously for 4 hours. Upon completion of the reaction, tetrahydrofuran (20 mL) was added, followed by the addition of cation-exchange resin to adjust the pH to be acidic. The mixture was stirred continuously for another 2 hours, and filtered. The resulting filtrate was directly added with 10% Pd/C (0.2 g) without concentration and hydrogenated. The reaction was run at 25° C. for 24 hours, and filtered. The resulting filtrate was concentrated and evaporated to give 0.46 g of M14 as a yellowish solid with overall 98% yield of the two steps aforementioned.

$^1$H NMR (500 MHz, DMSO-$d_6$) δ=12.61 (s, 1H), 10.83 (s, 1H), 9.07 (s, 2H), 8.88 (s, 1H), 7.19 (s, 2H), 6.36 (d, J=1.9 Hz, 1H), 6.19 (d, J=1.9 Hz, 1H), 5.33 (d, J=7.1 Hz, 1H), 5.03 (s, 1H), 4.88 (s, 1H), 4.63 (s, 1H), 4.61 (s, 1H), 4.57 (s, 1H), 4.45 (s, 3H), 3.69-3.62 (m, 3H), 3.56 (d, J=5.5 Hz, 2H), 3.52 (m, J=6.6 Hz, 3H), 3.44 (d, J=6.9 Hz, 2H), 3.40 (s, 2H). $^{13}$C NMR (500 MHz, DMSO-$d_6$) δ=177.33, 164.12, 161.24, 156.25, 156.20, 145.39 (2C), 136.72, 133.72, 119.97, 108.56 (2C), 103.91, 102.01, 100.59, 98.67, 93.41, 74.10, 73.03, 72.90, 71.18, 70.92, 70.23, 67.74, 66.75, 61.05, 48.63.

Example 17

Determination of Therapeutic Effects of Myricetin Derivative M13 and M14 on DSS-Induced Chronic Colitis in Mice See Example 8 for the experimental method.

Figure 11:
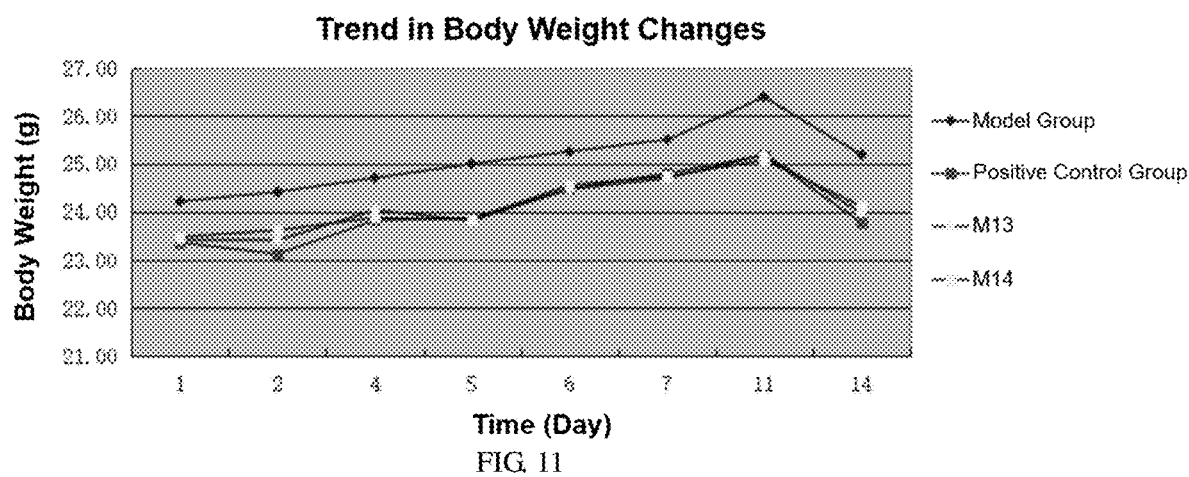
FIG. 11 illustrates the results of changes in body weight of each group of mice during drug administration in Example 17.
Figure 12:
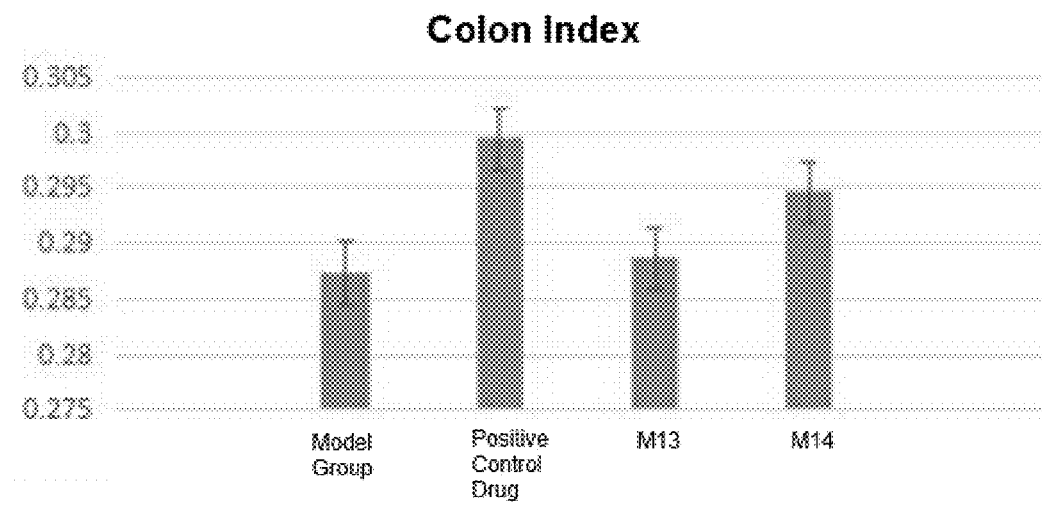
FIG. 12 illustrates the results of colon index (length/body weight) of each group of mice at the end of drug administration in Example 17.

The results of body weight changes in each group of mice during drug administration were shown in FIG. 11; the results of colon length in each group of mice were shown in FIG. 12; body weights and colon lengths of M13- and M14-treated mice were similar to those of positive control group, and were significantly increased compared to those of model group (P<0.05), indicating an inhibitory activity against chronic colon inflammation.

The above examples are only used to illustrate the technical solutions of the present invention, and are not limited thereto; although the present invention has been described in detail with reference to the foregoing examples, for those skilled in the art, the technical solutions described in the foregoing examples may be modified, or some of the technical features may be equivalently replaced; and such modifications or substitutions do not depart from the spirit and scope of the technical solutions claimed in the present invention.

The invention claimed is:

1. A myricetin derivative or a pharmaceutically acceptable salt thereof, selected from the group consisting of:

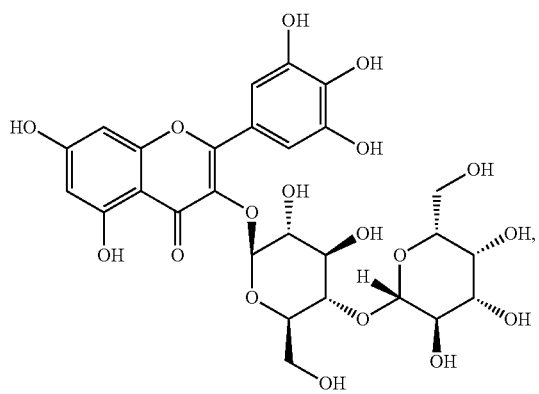

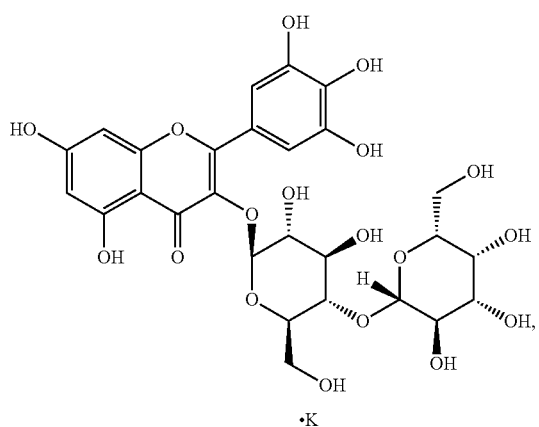

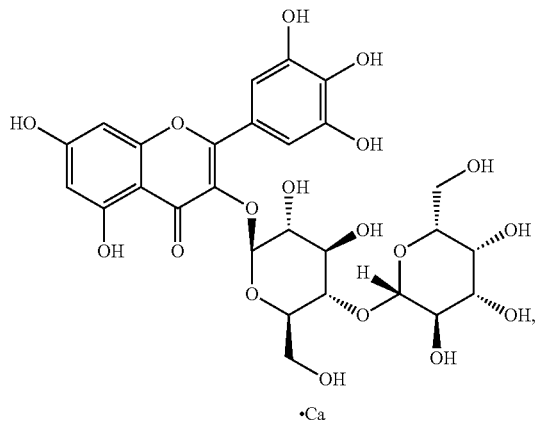

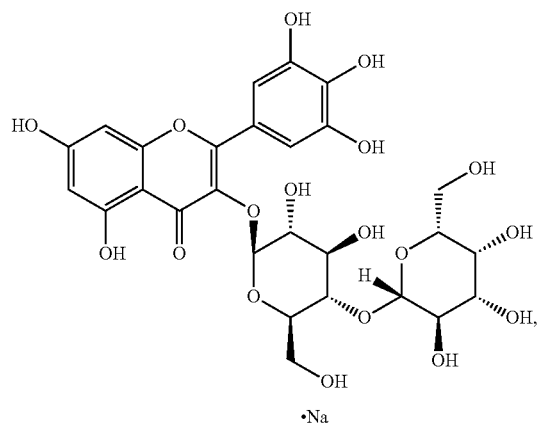
M10
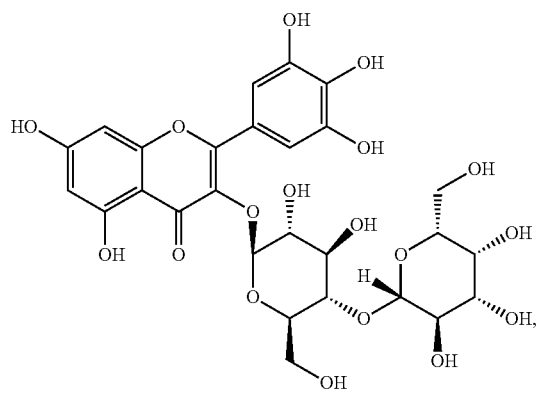
M7
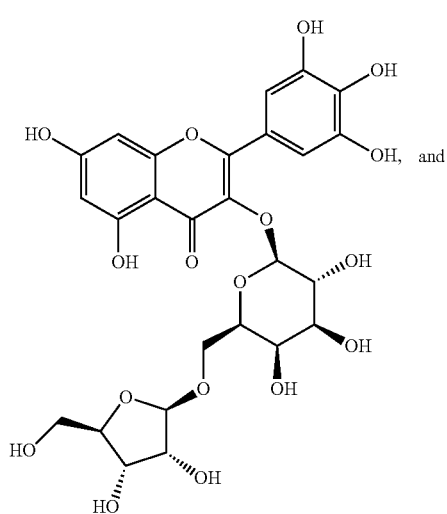
M13
and
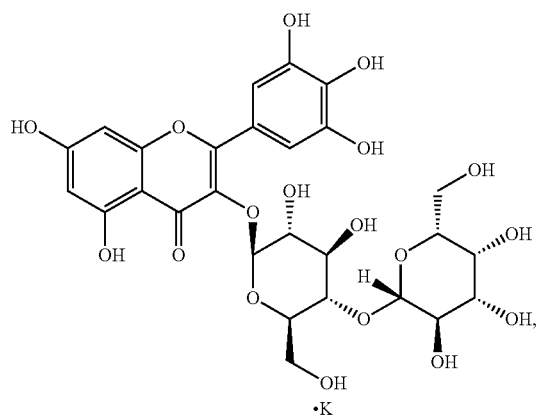
M8
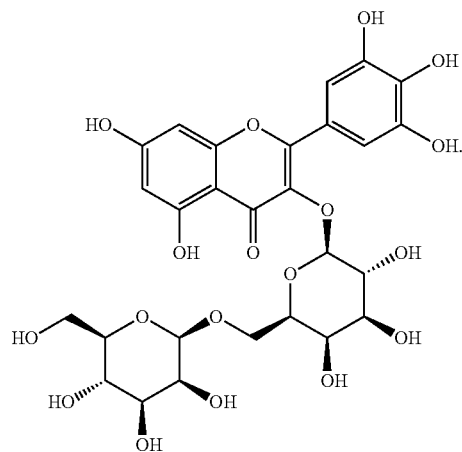
M14
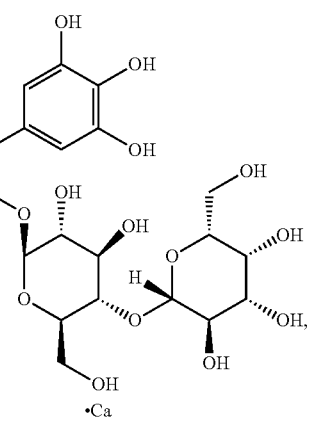
M9
or
2. The myricetin derivative or the pharmaceutically acceptable salt thereof according to claim 1, wherein the myricetin derivative or the pharmaceutically acceptable salt thereof is

M10

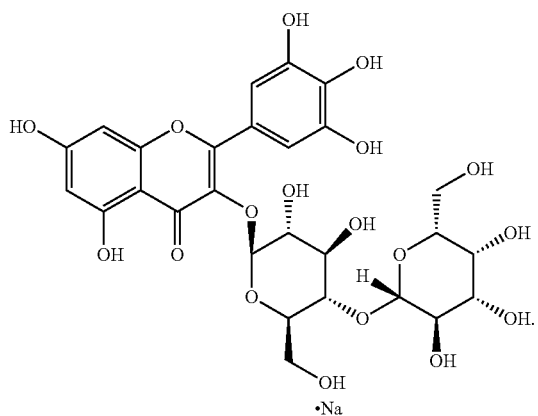
•Na

3. A pharmaceutical composition comprising the myricetin derivative or the pharmaceutically acceptable salt thereof according to claim 1 and a pharmaceutically acceptable carrier.

4. The pharmaceutical composition according to claim 3, wherein said pharmaceutically acceptable carrier is an alkaline substance comprising an alkaline adjuvant or solvent;
wherein said alkaline adjuvant is selected from the group consisting of sodium bicarbonate, potassium bicarbonate, sodium carbonate, sodium hydroxide, potassium hydroxide, sodium acetate, sodium octoate, sodium iso-octoate, sodium citrate, sodium tartrate, and the combination thereof;
and wherein said alkaline solvent is selected from the group consisting of sodium bicarbonate solution or sodium bicarbonate injection, sodium citrate solution or sodium citrate injection, sodium lactate solution or sodium lactate injection, compound sodium lactate-glucose solution or compound sodium lactate-glucose injection, sodium oxybate solution or sodium oxybate injection, sodium glutamate solution or sodium glutamate injection, potassium glutamate solution or potassium glutamate injection, and the combination thereof.

5. The pharmaceutical composition according to claim 4, wherein said alkaline adjuvant is sodium bicarbonate, potassium bicarbonate, or sodium hydroxide, and wherein said alkaline solvent is sodium bicarbonate solution or sodium bicarbonate injection.

6. A method of treating chronic colitis or colitis-associated tumorigenesis, comprising administering the myricetin derivative or the pharmaceutically acceptable salt thereof according to claim 1 to a subject in need thereof.

7. A method of treating a disease associated with endoplasmic reticulum stress comprising administering the myricetin derivative or the pharmaceutically acceptable salt thereof according to claim 1 to a subject in need thereof.

8. The method according to claim 7, wherein said disease associated with endoplasmic reticulum stress is chronic colitis.

9. The method according to claim 7, wherein administering the myricetin derivative or the pharmaceutically acceptable salt thereof modulates activities of an endoplasmic reticulum stress signaling molecule.

10. The method according to claim 9, wherein said endoplasmic reticulum stress signaling molecule is GRP78, ATF6, P-eIF-2α, IREα, ATG3, ATG5, ATG7, ATG12, or ATG1611.

11. The myricetin derivative or the pharmaceutically acceptable salt thereof according to claim 1, wherein the myricetin derivative or the pharmaceutically acceptable salt is:

M7

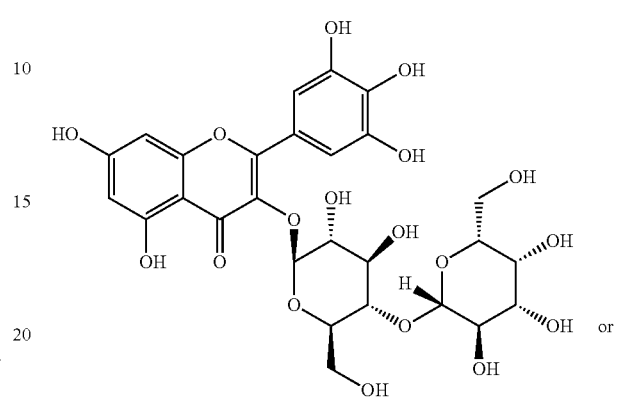
or

M10

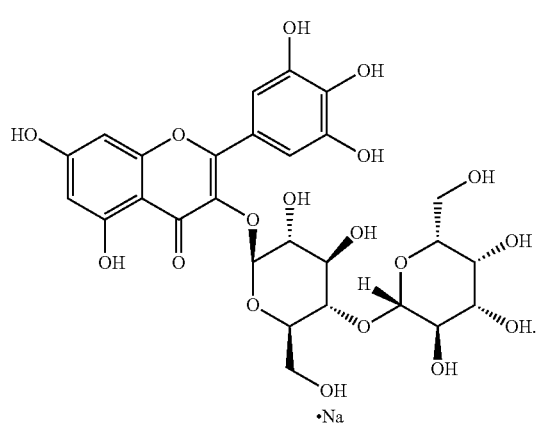
•Na

12. A method of preparing the myricetin derivative or the pharmaceutically acceptable salt thereof according to claim 2, comprising the steps of:

a) protecting phenolic hydroxyl groups at the C-7, C-3', C-4' and C-5' positions of starting material myricetrin M1, to form benzyl-protected myricetrin derivative M2;

b) removing the C-3 rhamnose from myricetrin M2 to form benzyl-protected myricetin derivative M3;

c) condensing benzyl-protected myricetin M3 with acetyl lactosyl-bromide M4, in the presence of an alkali, to obtain lactosyl derivative M5;

d) deprotecting the benzyl group from M5 by palladium-carbon catalysis to obtain acetyl-protected lactosyl derivative M6; or deprotecting the acetyl group from M5 in the presence of sodium methoxide to obtain benzyl-protected lactosyl derivative M6';

e) deprotecting the acetyl group from M6 in the presence of sodium methoxide to obtain M7; or deprotecting the benzyl group from myricetin derivative M6' by palladium-carbon catalysis to obtain M7; and f) reacting M7 with an alkali metal or alkaline earth metal to obtain M8, M9, or M10, wherein, structures of M1, M2, M3, M4, M5, M6, and M6' as shown below:

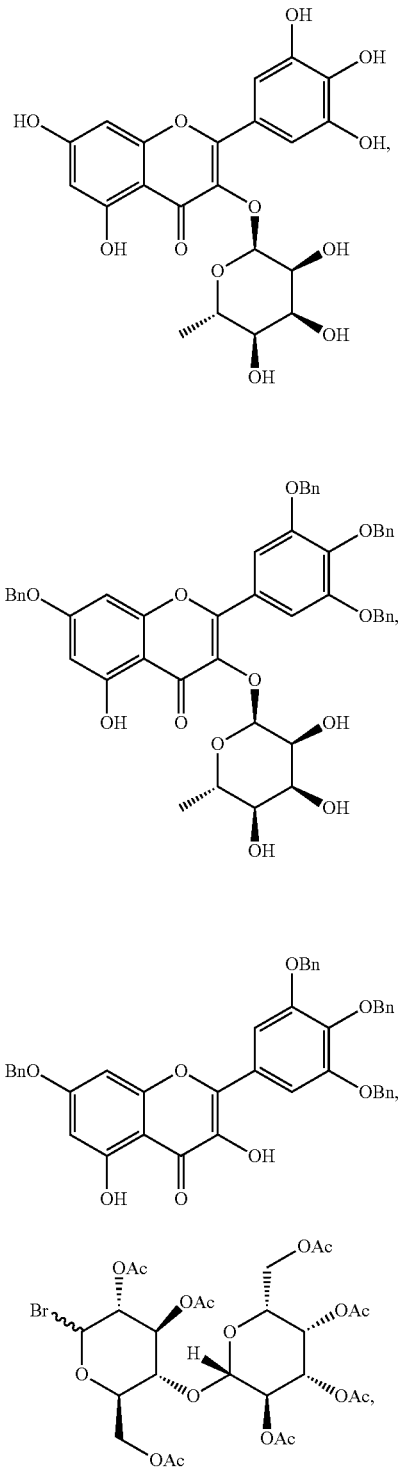
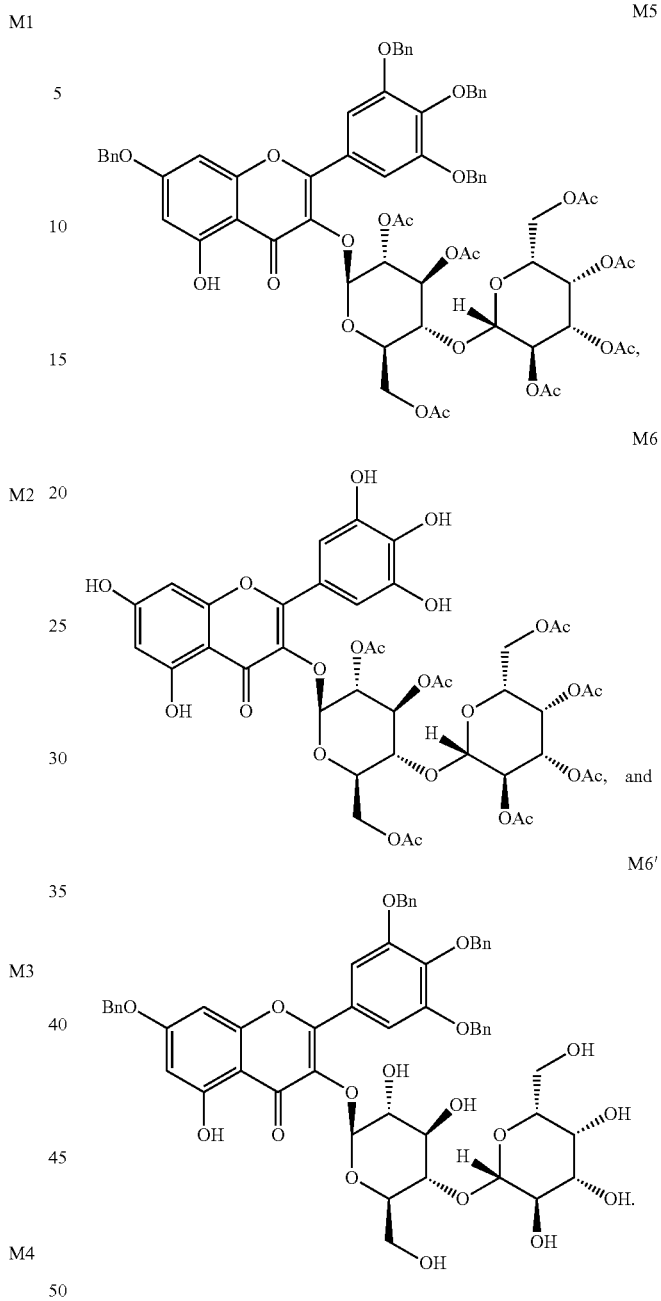
13. The method according to claim 12, wherein said alkali in step c) is selected from the group consisting of potassium carbonate, sodium carbonate, cesium carbonate, triethylamine, diisopropylethylamine, 4-dimethylaminopyridine, and the combination thereof.
14. The method according to claim 13, wherein said alkali is potassium carbonate.
* * * * *